United States Patent
Twetan et al.

(10) Patent No.: US 7,317,946 B2
(45) Date of Patent: Jan. 8, 2008

(54) TELEMETRY ANTENNA FOR AN IMPLANTABLE MEDICAL DEVICE

(75) Inventors: Len D. Twetan, Excelsior, MN (US); Piotr Przybyszewski, Coon Rapids, MN (US); Garry L. Dublin, Maple Grove, MN (US); Gregory J. Haubrich, Champlin, MN (US); Andrina J. Hougham, North Oaks, MN (US); Andrew J. Ries, Lino Lakes, MN (US); David B. Engmark, Bethel, MN (US); Gary M. Grose, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 275 days.

(21) Appl. No.: 10/797,511

(22) Filed: Mar. 10, 2004

(65) Prior Publication Data

US 2005/0203583 A1    Sep. 15, 2005

(51) Int. Cl.
*A61N 1/08* (2006.01)

(52) U.S. Cl. .................. 607/60; 607/32; 607/36; 607/55; 607/56; 607/57; 607/156; 128/903; 343/718; 343/824; 343/873; 340/527.7

(58) Field of Classification Search ............ 607/36–37, 607/55–57, 60, 32, 156; 128/903; 343/718, 343/873, 700 NS, 824; 340/527.7
See application file for complete search history.

(56) References Cited

U.S. PATENT DOCUMENTS

| 2002/0105467 A1* | 8/2002 | Haussler et al. ............ 343/702 |
| 2005/0134520 A1* | 6/2005 | Rawat et al. ............... 343/873 |
| 2005/0203584 A1* | 9/2005 | Twetan et al. ............... 607/36 |

\* cited by examiner

*Primary Examiner*—Carl Layno
*Assistant Examiner*—Deborah Malamud
(74) *Attorney, Agent, or Firm*—Daniel G. Chapik

(57) ABSTRACT

A telemetry antenna for an implantable medical device includes one or more portions having a non-linear configuration. In some embodiments, the non-linear configuration provides an antenna having a greater antenna length than the linear lengthwise dimension of the antenna structure. In some embodiments, the non-linear configuration is a serpentine pattern.

40 Claims, 21 Drawing Sheets

TELEMETRY ANTENNA FOR AN IMPLANTABLE MEDICAL DEVICE

FIELD OF THE INVENTION

The present invention relates generally to a telemetry antenna and methods of fabrication for an implantable medical device (IMD) including a telemetry antenna.

BACKGROUND OF THE INVENTION

A variety of implantable medical devices (IMD's) exist that provide diagnostic or therapeutic capabilities. These IMD's include, for example, cardiac pacemakers, implantable cardioverters/defibrillators (ICD's), and various tissue, organ and nerve stimulators or sensors. IMD's typically include their components within a hermetically sealed enclosure referred to as a "can" or housing. In some IMD's, a connector header or connector block is attached to the housing and allows interconnection with one or more elongated electrical medical leads.

The header is typically molded from of a relatively hard, dielectric, non-conductive polymer having a thickness approximating the housing thickness. The header includes a mounting surface that conforms to and is mechanically affixed against a mating sidewall surface of the housing.

It has become common to provide a communication link between the hermetically enclosed electronic circuitry of the IMD and an external programmer or monitor or other external medical device (herein an EMD unless otherwise identified) in order to provide for downlink telemetry (DT) transmission of commands from the external device to the IMD and to allow for uplink telemetry (UT) transmission of stored information and/or sensed physiological parameters from the IMD to the EMD. As the technology has advanced, IMDs have become ever more complex in possible programmable operating modes, menus of available operating parameters, and capabilities of monitoring increasing varieties of physiologic conditions and electrical signals which place ever increasing demands on the programming system. Conventionally, the communication link between the IMD and the EMD is by encoded RF transmissions between an IMD RF telemetry antenna and transceiver and an EMD RF telemetry antenna and transceiver.

The telemetry transmission system that evolved into current common use relies upon the generation of low amplitude magnetic fields by current oscillating in an LC circuit of an RF telemetry antenna in a transmitting mode and the sensing of currents induced by a closely spaced RF telemetry antenna in a receiving mode. Short duration bursts of the carrier frequency are transmitted in a variety of telemetry transmission formats. In some products, the RF carrier frequency is set at 175 kHz, and the RF telemetry antenna is coiled wire wound about a ferrite core. The EMD is typically a programmer having a manually positioned programming head having an external RF telemetry antenna. Generally, the antenna is disposed within the hermetically sealed housing; however, the typically conductive housing adversely attenuates the radiated RF field and limits the data transfer distance between the programmer head and the IMD RF telemetry antennas to a few inches.

The above described telemetry system employing the 175 kHz carrier frequency limits the upper data transfer rate, depending on bandwidth and the prevailing signal-to-noise ratio. Using a ferrite core/wire coil, RF telemetry antenna results in: (1) a very low radiation efficiency because of feed impedance mismatch and ohmic losses; 2) a radiation intensity attenuated proportionally to at least the fourth power of distance (in contrast to other radiation systems which have radiation intensity attenuated proportionally to square of distance); and 3) good noise immunity because of the required close distance between and coupling of the receiver and transmitter RF telemetry antenna fields.

With these characteristics, the IMD is subcutaneously and preferably oriented with the RF telemetry antenna closest to the patient's skin. To ensure that the data transfer is reliable, the programming head and corresponding external antenna are positioned relatively close to the patient's skin.

It has been recognized that "far field" telemetry, or telemetry over distances of a few too many meters from an IMD would be desirable. Various attempts have been made to provide antennas with an IMD for facilitate far field telemetry. Many proposals have been advanced for eliminating the ferrite core, wire coil, RF telemetry antenna and substituting alternative telemetry transmission systems and schemes employing far higher carrier frequencies and more complex signal coding to enhance the reliability and safety of the telemetry transmissions while increasing the data rate and allowing telemetry transmission to take place over a matter of meters rather than inches. A wide variety of alternative IMD telemetry antennas mounted outside of the hermetically sealed housing have been proposed. These approaches are generally undesirable in that depending upon the option selected they require substantial modification of the housing and/or heading, require additional components added to the housing (e.g., dielectric shrouds about a portion of the housing), reduce the effectiveness of other components (e.g., reducing the surface area available for use as a can electrode), create a directional requirement (e.g., require that the IMD be oriented in a particular direction during implant for telemetry effectiveness), or finally that they add extraneous exposed components that are subject to harmful interaction in the biological environment or require additional considerations during implant (e.g., stub antennas extending outward from the device).

It remains desirable to provide a telemetry antenna for an IMD that eliminates drawbacks associated with the IMD telemetry antennas of the prior art. As will become apparent from the following, the present invention satisfies this need.

DETAILED DESCRIPTION

The present invention relates to providing an improved RF telemetry antenna disposed outside a hermetically sealed housing of an IMD. The following description provides various embodiments in the context of an ICD. However, the present invention is intended to be implemented with a wide variety of IMD's.

The IMD telemetry antenna has two primary functions: to convert the electromagnetic power of a DT transmission of an EMD telemetry antenna propagated through the atmosphere and then through body tissues into a UHF signal that can be processed by the IMD transceiver into commands and data that are intelligible to the IMD electronic operating system; and to convert the UT UHF signals of the IMD transceiver electronics into electromagnetic power propagated through the body tissue and the atmosphere so that the EMD can receive it.

Figure 1:
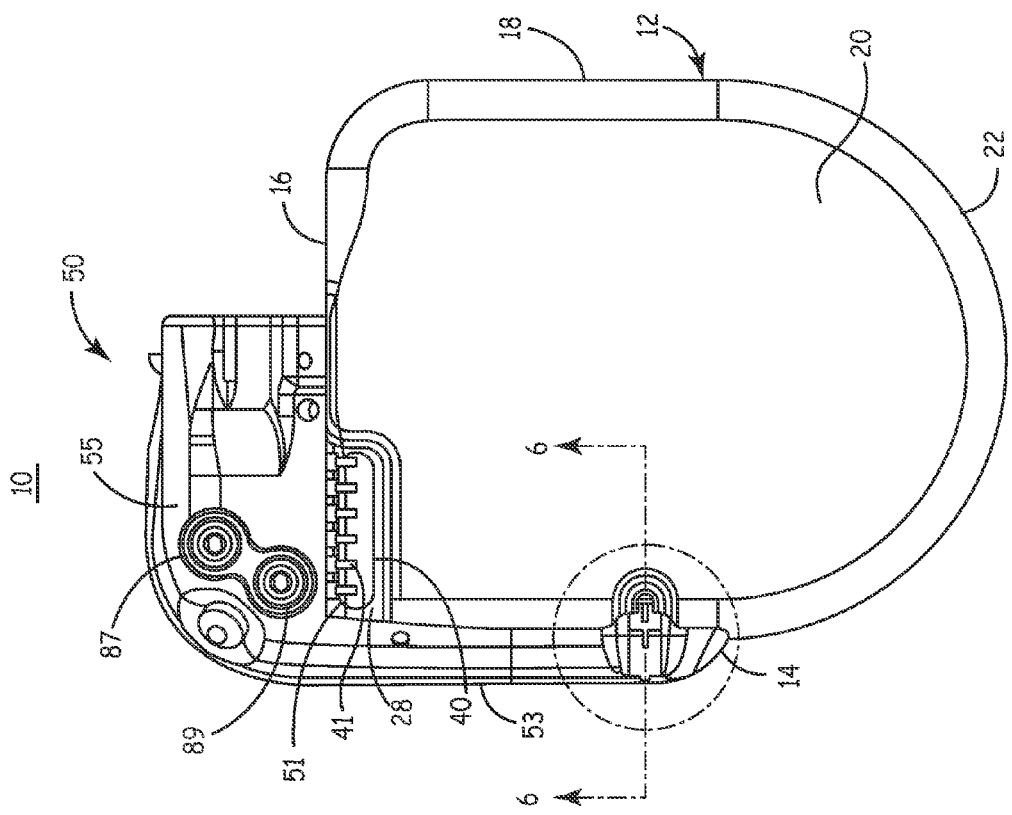
FIG. 1 is a plan view of a first embodiment of an ICD fabricated with an elongated IMD antenna within the connector header in accordance with a first embodiment of the invention.

In the embodiment illustrated in FIG. 1, a first IMD telemetry antenna element is supported to extend in a first direction along a first minor side of a substantially rectilinear, conductive IMD housing, and a second antenna element is supported to extend in a second direction along a second minor side of the substantially rectilinear, conductive IMD housing. The first and second antenna elements are supported to extend apart at substantially 90° to one another, i.e., substantially orthogonally, in substantially a common plane to optimize UT transmission and DT reception by at least one of the first and second antenna elements depending upon the spatial orientation of the IMD antenna elements to similar EMD antenna elements.

An ICD 10 includes a hermetically sealed housing 12 and a connector header 50. A set of ICD leads having cardioversion/defibrillation electrodes and pace/sense electrodes disposed in operative relation to a patient's heart are adapted to be coupled to the connector header 50 in a manner well known in the art. The ICD 10 is adapted to be implanted subcutaneously in the body of a patient such that the first and second orthogonally disposed IMD telemetry antenna elements are encased within body tissue and fluids including epidermal layers, subcutaneous fat layers and/or muscle layers.

Figure 6:
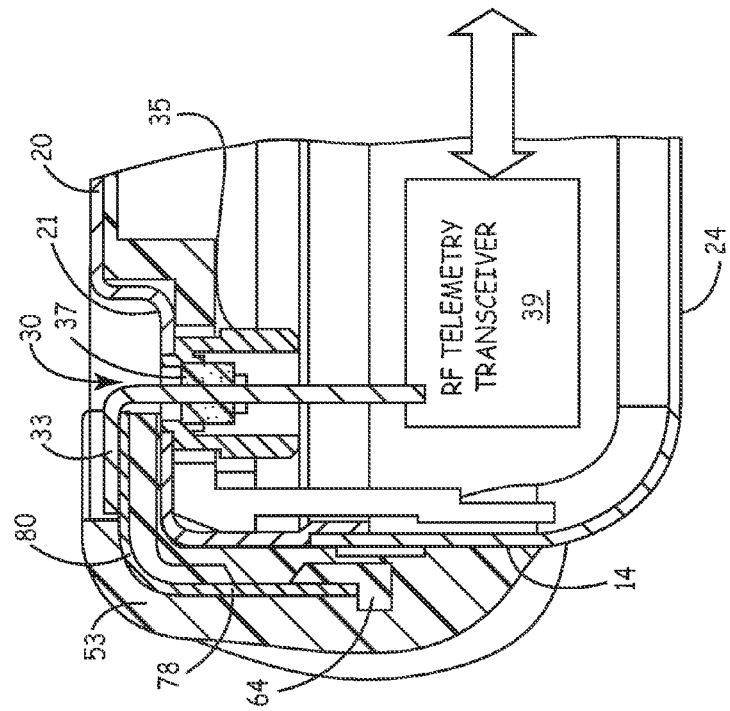
FIG. 6 is an enlarged cross-section view taken along lines 6-6 in FIG. 1 depicting the attachment of the external end of the antenna feedthrough pin to a welding tab of the telemetry antenna wire strip and the internal end of the antenna feedthrough pin to schematically depicted RF transceiver circuitry of the ICD.

The hermetically sealed housing 12 is generally circular, elliptical, prismatic or rectilinear having substantially planar major sides 20 and 24 joined by perimeter sides comprising substantially straight first minor side 14, second minor side 16, and third minor side 18 and a curvilinear fourth minor side 22. The first and second minor sides 14 and 16 are joined at a mutual corner or side junction 15. The hermetically sealed housing 12 is typically formed of a thin-walled biocompatible metal, e.g., titanium, shaped half sections that are laser seam welded together in a seam extending around the minor sides 14, 16, 18 and 22. A telemetry recess 21 is formed into the planar major side 20 adjacent first minor side 14 that includes a telemetry feedthrough hole that a telemetry antenna feedthrough 30 described further below with reference to FIG. 6 is welded into. A connector recess 23 is formed into the planar major side 20 adjacent to second minor side 16 that includes an elongated feedthrough hole that accommodates a single, elongated, feedthrough 40 supporting a plurality of feedthrough pins 41. A connector tab 32 extends away from the first housing side 14, and connector tabs 32, 34, 36 extend away from the second housing side 16.

The hermetically sealed housing 12 is often manufactured as an assembly or attachment with the separately fabricated connector header 50. One or more battery, high voltage output capacitor, and IC package, and other components are assembled in spacers and disposed within the interior cavity of housing 12 prior to seam welding of the housing halves. In the manufacturing process, electrical connections are made between IC connector pads or terminals with the inner ends of the connector header feedthrough pins. An electrical connection is also made between the inner end of the antenna feedthrough pin of antenna feedthrough 30 and the telemetry transceiver circuit as described further below in reference to FIG. 6.

The connector header 50 is also formed as a separate assembly comprising a first header segment 53 and a second header segment 55 having substantially contiguous header segment sides 54 and 56, respectively, that are shaped to fit against the contiguous first and second minor sides 14 and 16 and to receive connector tabs 32, 34, 36 and 38. The connector header 50 is mechanically fixed to the first and second minor sides 14 and 16 by use of pins or screws 42, 44, 46, and 48 that fit through aligned holes in connector header 50 and the respective connector tabs 32, 34, 36, and 38. The connector header 50 is also formed with an array of connector header electrical pads 51 that fit into the telemetry recess 21. As shown in FIG. 1, each of the connector feedthrough pins 41 are bent over and welded to a respective one of the electrical pads 51. After testing, the telemetry recess 21 is filled with biocompatible medical adhesive or epoxy to cover and electrically insulate the welded together connector feedthrough pins 41 and electrical pads 51 from body fluids.

Figure 4:
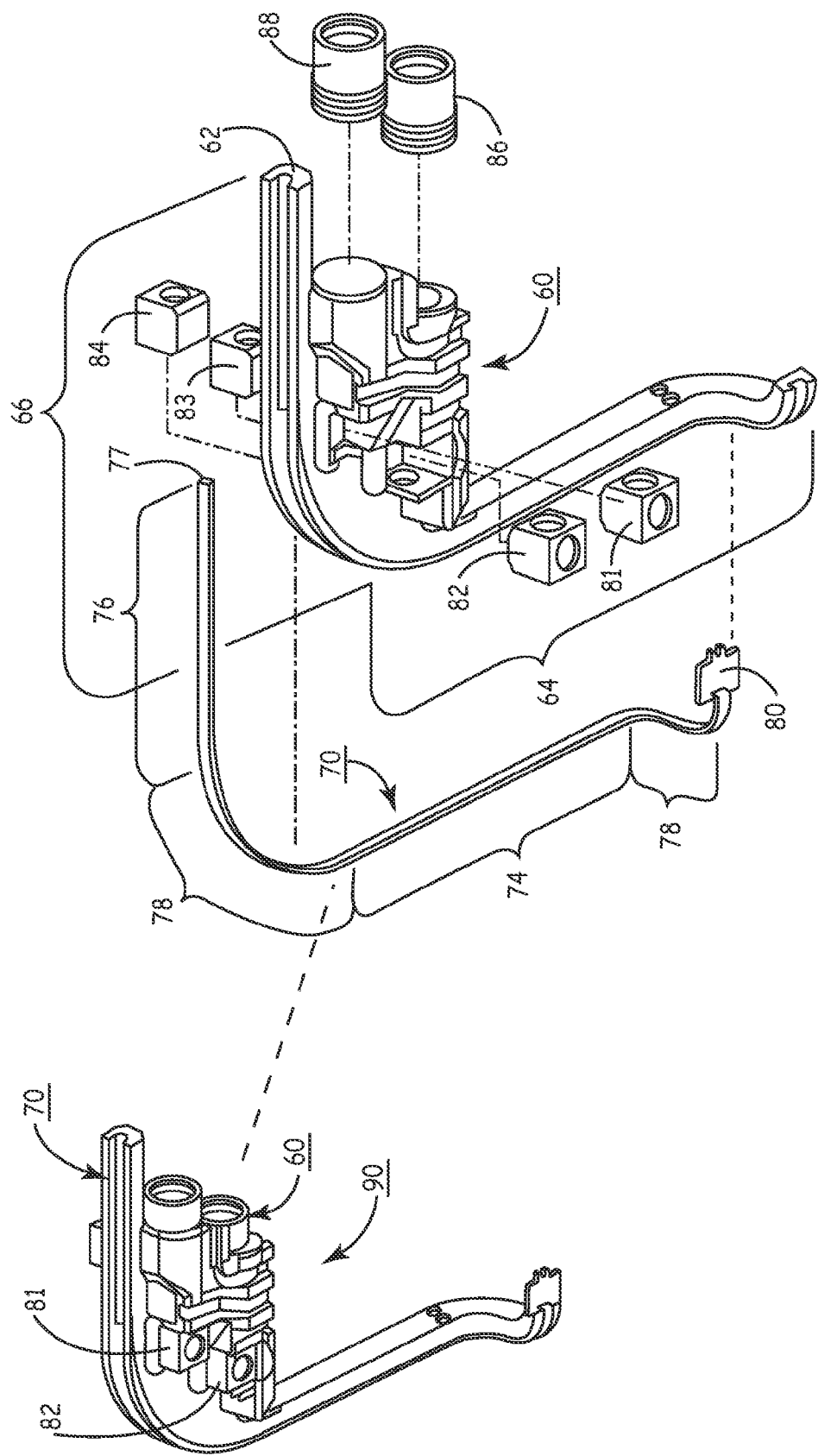
FIG. 4 is an exploded perspective view of an undermold supporting the elongated IMD telemetry antenna as well as connector blocks, and connector rings employed in a connector header having four connector bores accepting two unipolar and two bipolar lead connector assemblies.

Referring to FIG. 4, the elongated IMD telemetry antenna 70 comprises a wire strip bent at substantially 90° bend 72 into orthogonally extending first and second telemetry antenna elements 74 and 76. The second telemetry antenna element 76 extends from the substantially 90° bend 72 to a wire strip free end 77. The first telemetry antenna element 74 extends from the substantially 90° bend 72 to a lateral wire strip bend 78 over to a wire strip fixed end at connector pad 80.

In this embodiment, the connector header 50, including the first and second header segments 53 and 55, is formed of an integral undermolded frame or "undermold" 60 formed of polymer, e.g., polyurethane, that supports the wire strip IMD telemetry antenna 70 and the depicted connector header components. A polymeric overmold 57 is molded over the sub-assembly of the telemetry antenna and the connector header components, thereby sealing the sub-assembled components and providing a radome over the wire strip telemetry antenna. The connector header 50 is then assembled to the hermetically sealed housing 12, and the telemetry antenna fixed end is electrically connected to the telemetry transceiver.

More particularly, the undermold 60 is molded having first and second undermold segments 64 and 66. An outer channel 62 of the undermold 60 extends through the first and second undermold segments 64 and 66 and is shaped to the shape of the wire strip telemetry antenna 70 as shown in FIG. 4. The first undermold segment 64 is also shaped to define connector bores and to support header connector elements 81, 82, 83, 84, 86 and 88. The header connector elements 81, 82, 83, 84 receive the proximal connector pins of cardiac leads inserted into the connector bores and comprise conventional setscrews accessed through penetrable silicone rubber setscrew grommets, e.g., grommets 87 and 89 of FIG. 1, to tighten the lead connector pins in place in a manner well known in the art. The tubular connector rings 86 and 88 include inwardly extending resilient force beams that bear against connector rings of bipolar lead connector assemblies of cardiac leads inserted into connector bores in a manner well known in the art. The undermold 60 and wire strip telemetry antenna 70 are assembled together to form the undermold sub-assembly 90 depicted in FIGS. 4 and 5. It will be understood that the terminals of conductors of a conductor assembly (not shown) are also welded to the connector elements 81, 82, 83, 84, 56 and 88 and terminate in the connector pad array 51 depicted in FIG. 1.

A polymeric overmold 57 is then molded from a suitable polymer, e.g., a medical grade polyurethane, over the undermold sub-assembly 90. The overmold 57 defines various features of the connector header 50 that are not important to the practice of the present invention, including the outer contours, the connector bore openings, suture holes, and attachment bore openings, setscrew access openings, etc. In this regard, it should be noted that the overmold 57 is molded to define an inner bipolar connector bore aligned with the connector block 82 and connector ring 86 for receiving a first bipolar lead connector pin and ring. Similarly, the overmold 57 is molded to define an outer bipolar connector bore aligned with the connector block 81 and connector ring 88 for receiving a second bipolar lead connector pin and ring. The overmold 57 is also molded to define inner and outer unipolar connector bores that are aligned with the connector blocks 83 and 84, respectively, to receive first and second unipolar lead connector pins. The number, types and particular configurations of the lead connector elements and connector bores are not important to the practice of the present invention.

Figure 5:
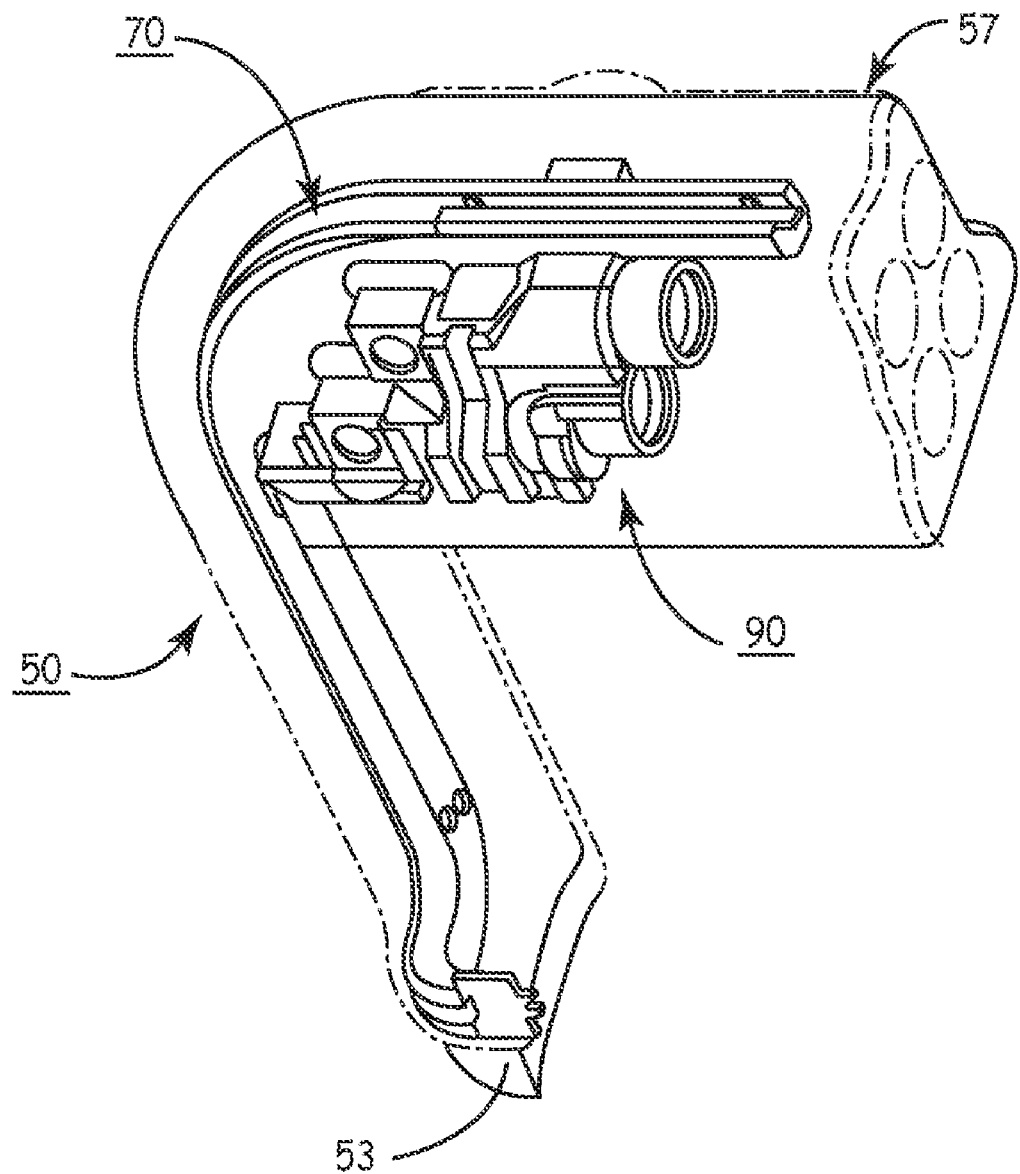
FIG. 5 is a perspective view of an overmold molded over the assembly of the undermold, connector blocks, sealing rings, and the elongated IMD telemetry antenna of FIG. 4.
Figure 7:
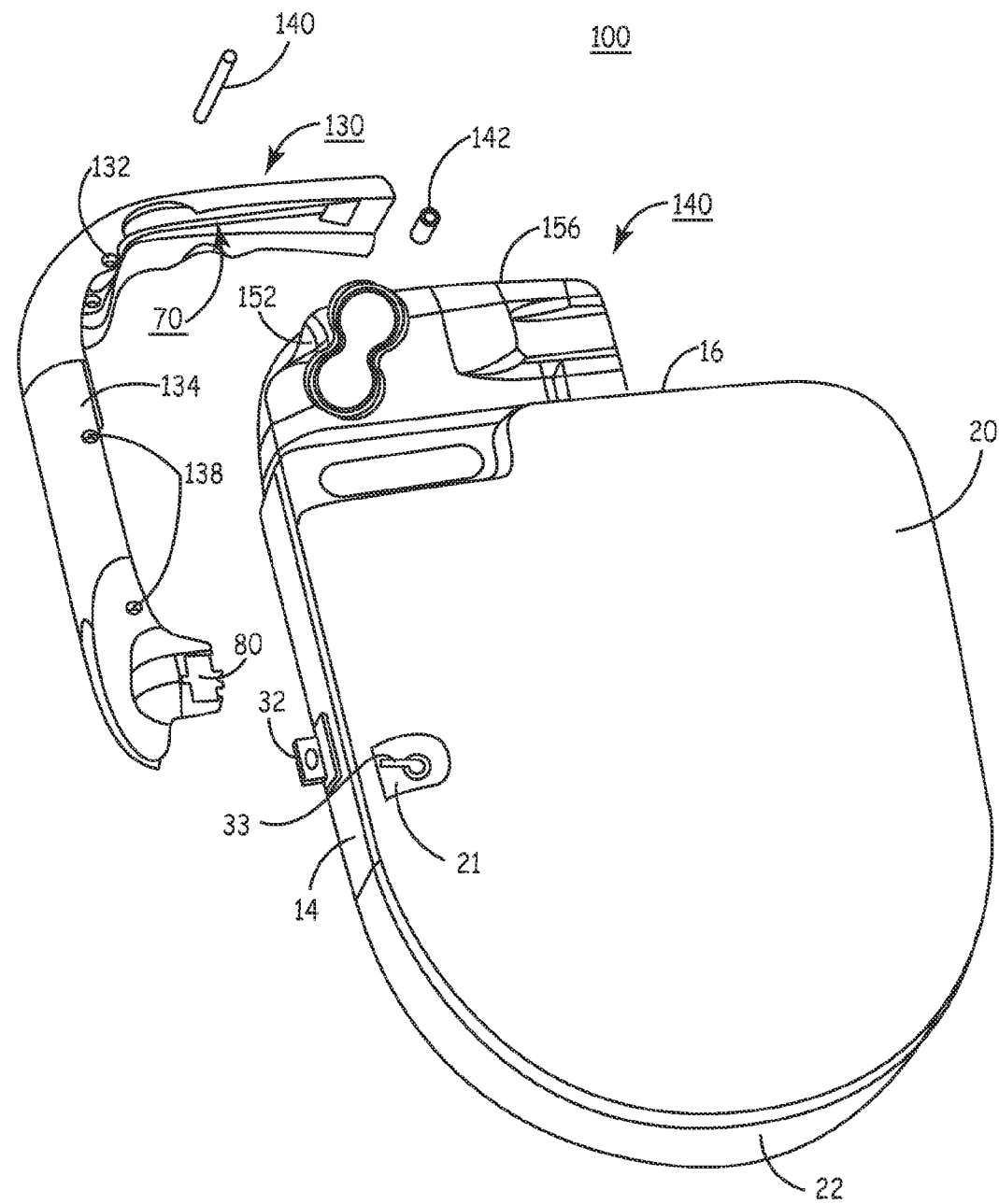
FIG. 7 is a perspective exploded front view of a second embodiment of the invention affixing an IMD telemetry antenna within an adaptor connector module to an ICD having a conventionally formed connector header in accordance with a second embodiment of the invention.

More importantly, overmold 57 and the undermold 60 do define the shapes of the header sides 54 and 56 that match the shapes of the housing minor sides 14 and 16, respectively. The overmold 57 also seals the telemetry antenna 70 within the undermold channel 62, except for the outer surface of the antenna connector pad 80, which is left exposed as shown in FIG. 5. The overmold 57 thereby seals the assembled components of undermold sub-assembly 90, and provides a radome over the first and second, wire strip, antenna elements 74 and 76 of antenna 70 and otherwise electrically insulates the telemetry antenna 70 from body tissue and fluid. The connector header pad array 51 is also left exposed by the overmold 57 to enable attachment to the connector feedthrough pins 41 as described above. As noted above, the attachment of the connector header 50 to the hermetically sealed housing 12 is effected using the pins or screws 42, 44, 46, and 48. Medical adhesive or epoxy is also typically injected through fill holes in the overmold 57 into interior spaces and gaps to seal the assembly and enhance adhesion of the connector header to the first and second minor sides 14 and 16.

As shown in FIG. 6, the feedthrough 30 comprises a ferrule 35 supporting a non-conductive glass or ceramic (e.g., alumina) annular insulator, that in turn supports and electrically isolates the feedthrough pin 33 from the ferrule 35. During assembly of the hermetically sealed housing 12, the ferrule 35 is welded to a feedthrough opening or hole through the housing major side 20 within the telemetry recess 21. The RF telemetry transceiver 39 (depicted schematically in FIG. 6) is electrically connected to the inner end of the antenna feedthrough pin 33. The connection of the RF telemetry transceiver 39 to the inner end of the antenna feedthrough pin 33 can be made in a variety of ways as by welding the inner end of the antenna feedthrough pin 33 to a substrate pad or clipping the inner end of the antenna feedthrough pin 33 to a cable or flex wire connector extending to a substrate pad or connector. The inner end of the antenna feedthrough pin 33 is electrically coupled to RF transceiver circuitry 39 disposed in close proximity thereto, in a manner that advantageously facilitates impedance matching and reduces losses.

The electrical connection is made between the antenna fixed end at antenna connector pad 80 with the outer end of the antenna feedthrough pin 33 of antenna feedthrough 30 after the antenna connector pad 80 is slipped laterally into the telemetry recess 21 such that the outer extending portion of the feedthrough pin 33 fits into a notch in the leading edge of the antenna connector pad 80 during assembly of the connector header 50 with the hermetically sealed housing 12. As shown in FIG. 6, the outer extending portion of the feedthrough pin 33 is bent over the exposed outer surface of the antenna connector pad 80 and laser welded thereto. The feedthrough pin outer end and the wire strip fixed end are laser welded together in a low profile weld within the telemetry recess 21 formed in the housing major side 20. After testing, the telemetry recess 21 is filled with medical adhesive or epoxy to cover and electrically insulate the bent over, outer extending portion of the feedthrough pin 33 and the exposed outer surface of the antenna connector pad 80.

Thus, the telemetry antenna 70 comprising the orthogonally disposed first and second antenna elements 74 and 76 is enclosed within and supported by the integrally formed connector header 50. The wire strip telemetry antenna 70 is attached to the outer end of the antenna feedthrough pin 33 that extends through the wall of the hermetically sealed housing 12 at a distance from the second header segment 55, thereby not interfering with the mechanical and electrical connections and components therein and allowing the wire strip antenna free end 77 to be displaced from the second minor side 16.

In another embodiment of the invention, an ICD 100 is depicted in FIGS. 6-9 and comprises the previously described hermetically sealed housing 12 providing the telemetry antenna feedthrough 30 mounted to the housing side 20 within telemetry recess 21 and electrically connected to the telemetry transceiver circuit 39 as depicted in FIG. 6. However, a conventional, pre-formed, connector header 140 is separately fabricated and affixed to the pre-formed hermetically sealed housing 12 following conventional fabrication techniques. The pre-formed connector header 140 depicted in FIG. 7 that is already attached to the second minor side 16 conforms in configuration, internal components and assembly to the second minor side 16 as described above with respect to the second header segment 56 of connector header 50. Details, e.g., the connector feedthrough pins 41 and tabs 51 that would be within recess 23 and the penetrable setscrew grommets, are not shown in all of FIGS. 7-9 to simplify the illustration.

Figure 8:
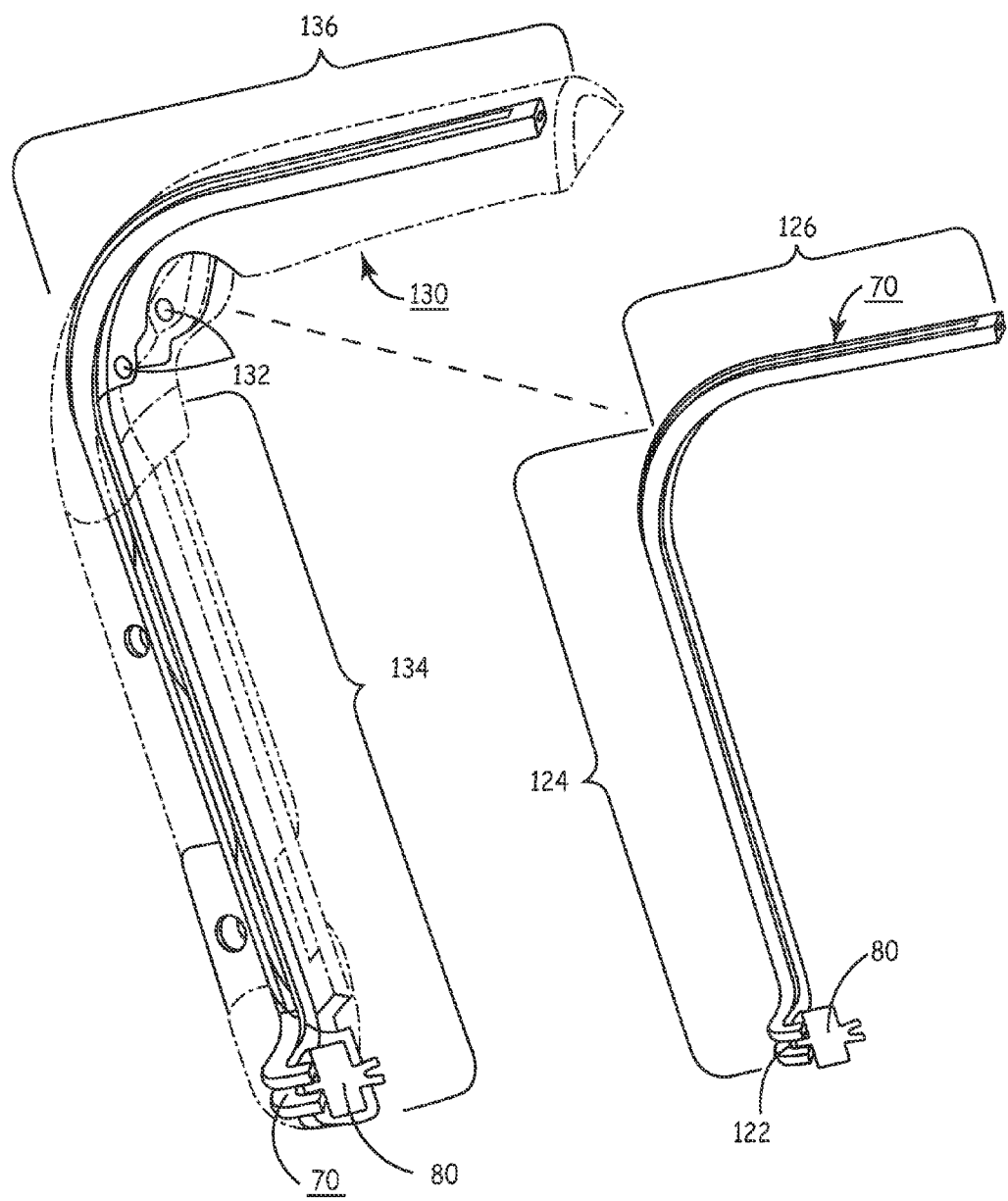
FIG. 8 is an exploded view of the wire strip in relation to the adaptor connector module of the second embodiment of the invention.
Figure 9:
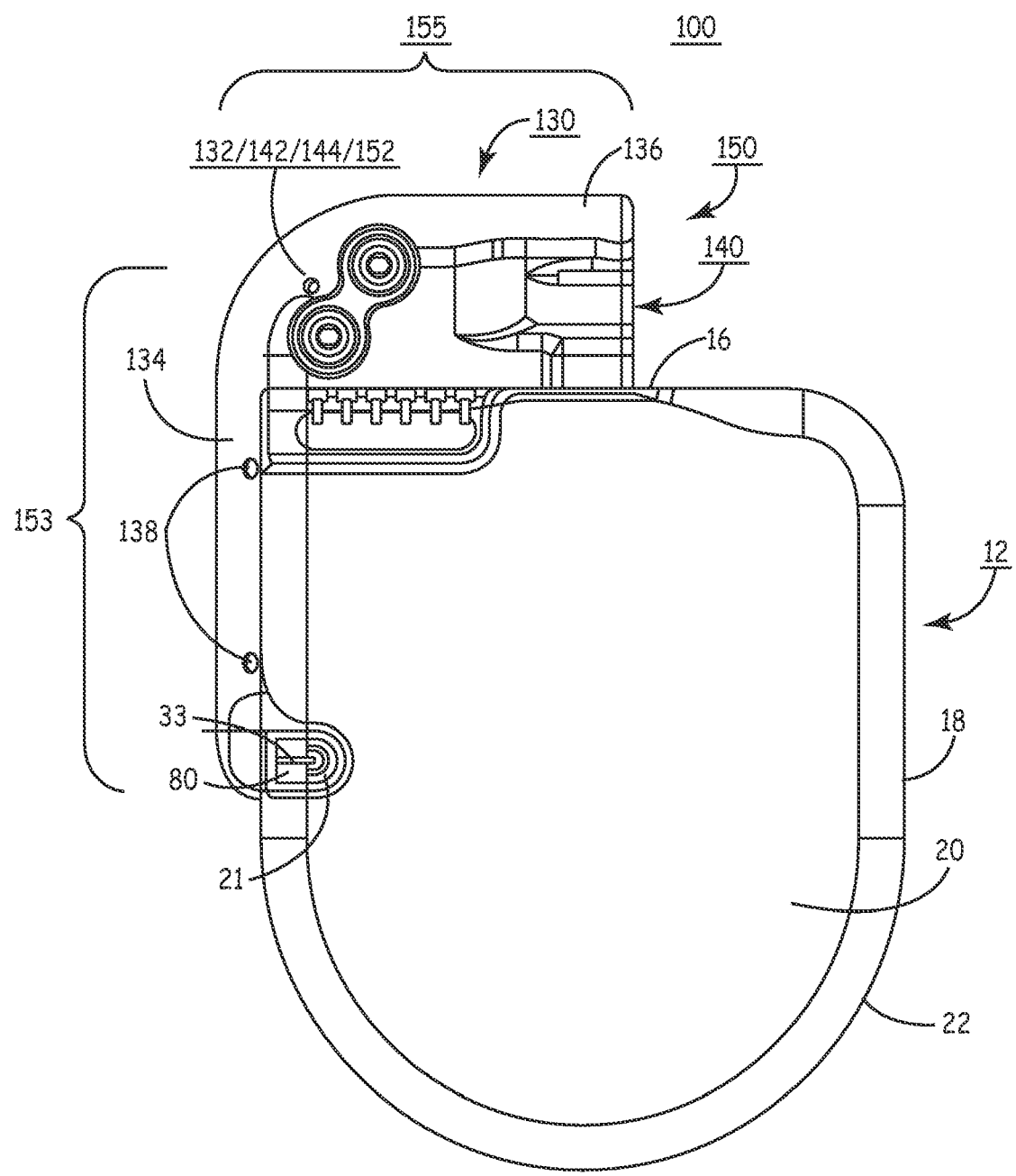
FIG. 9 is a plan view of the wire strip and adaptor connector module assembled to the ICD in accordance with the second embodiment of the present invention.

In this embodiment, as illustrated in FIG. 8, the telemetry antenna 70 is supported within a conforming channel 122 of a further undermold 120, and the assembly of undermold 120 and telemetry antenna 70 is embedded within a further overmolded antenna connector module 130. The further undermold 120 comprises a first undermold segment 124 supporting the first telemetry antenna element 74 and a second undermold segment 126 supporting the second telemetry antenna segment 76. The antenna connector module 130 similarly comprises a first overmolded module segment 134 encasing and providing a radome for the first telemetry antenna element 74 and a second overmolded module segment 136 encasing and providing a radome for the second telemetry antenna segment 76.

Figure 2:
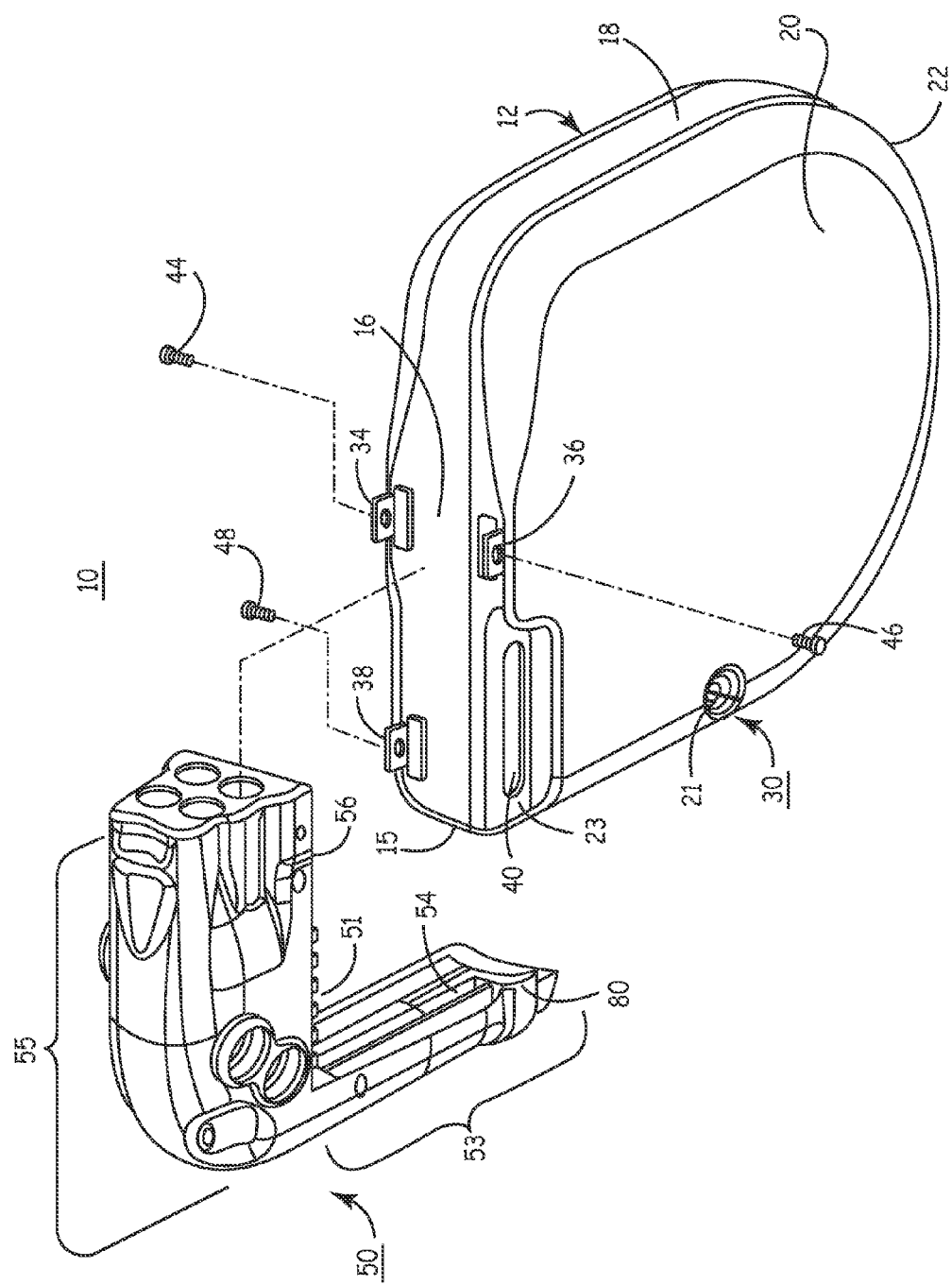
FIG. 2 is an exploded front perspective view of the ICD of FIG. 1 depicting the connector header disposed in relation to the ICD housing.
Figure 3:
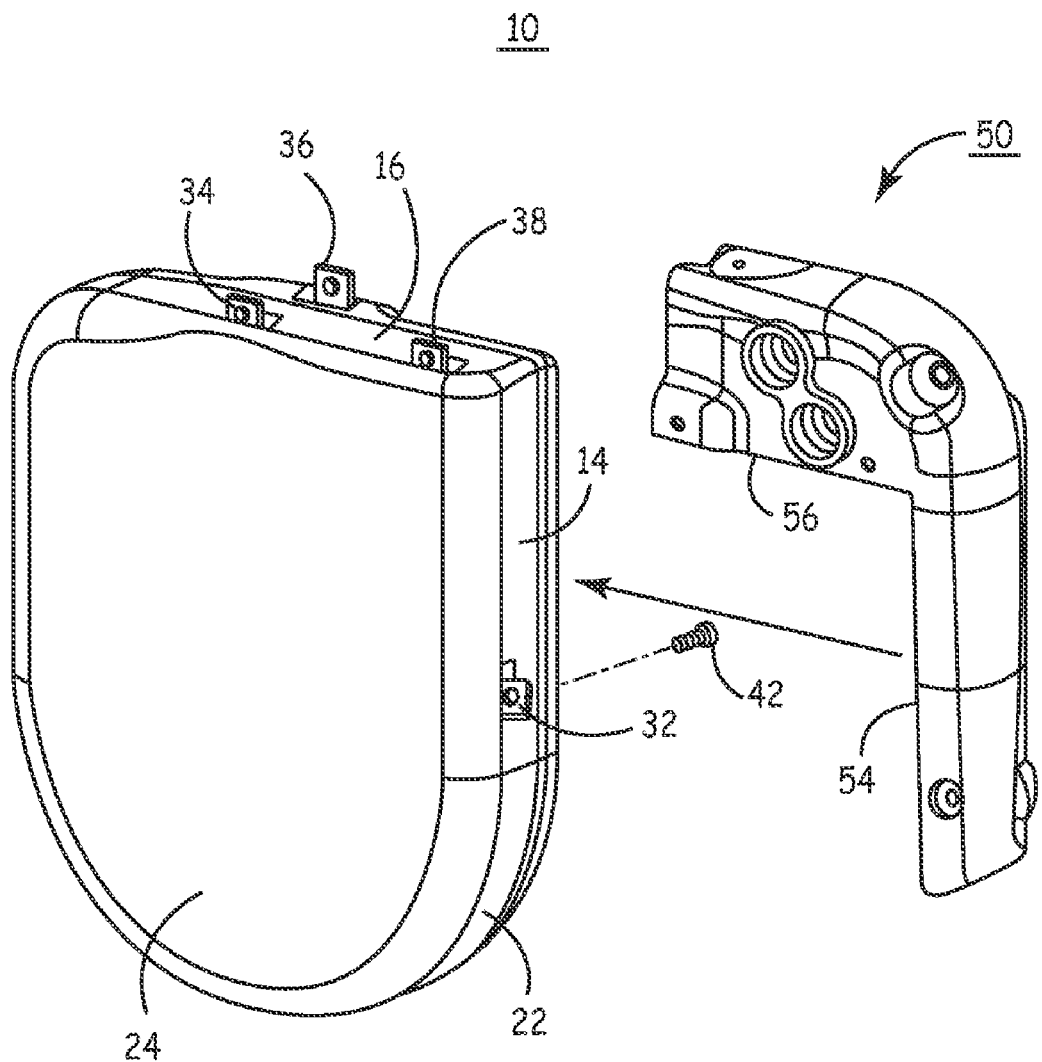
FIG. 3 is an exploded rear perspective view of the ICD of FIG. 1 depicting the connector header disposed in relation to the ICD housing.

The first and second overmolded module segments 134 and 136 are shaped and dimensioned to bear against the first minor side 14 and the outer header surface 156 of the pre-formed connector header 140, respectively. The antenna connector module 130 is formed with a bore 132 that is aligned with a suture hole 152 of the connector bore when the antenna connector module 130 is disposed against the first minor side 14 and the header outer surface 156. An adaptor sleeve 142 is fitted into the suture hole 152, and an adaptor pin 144 is fitted through the aligned bore 132 and adaptor sleeve 12 fitted into the suture hole 152 to fix the antenna connector module 130 to the pre-formed connector header 140. In addition, the adaptor connector module 130 is shaped with an intersecting slot and bore (not shown) that receives the connector tab 32 and titanium pin 42 (shown in FIG. 2) of the hermetically sealed housing 12. Moreover, medical adhesive or epoxy can be injected through a plurality of adhesive ports 138 into the gaps between the first and second overmolded module segments 134 and 136 and the first minor side 14 and the outer surface 156 of the pre-formed connector header 140, respectively.

Again, the antenna connector pad 80 is slipped laterally into the telemetry recess 21 such that the outer extending portion of the feedthrough pin 33 fits into a notch in the leading edge of the antenna connector pad 80 during assembly of the connector header 50 with the hermetically sealed housing 12 as shown in FIG. 6. The outer extending portion of the feedthrough pin 33 is bent over the exposed outer surface of the antenna connector pad 80 and welded thereto. After testing, the telemetry recess 21 is filled with medical adhesive or epoxy to cover and electrically insulate the bent over, outer extending portion of the feedthrough pin 33 and the exposed outer surface of the antenna connector pad 80. Upon completion of the assembly, a composite connector header 150 is formed effectively comprising first and second header segments 153 and 155, respectively.

Figure 10:
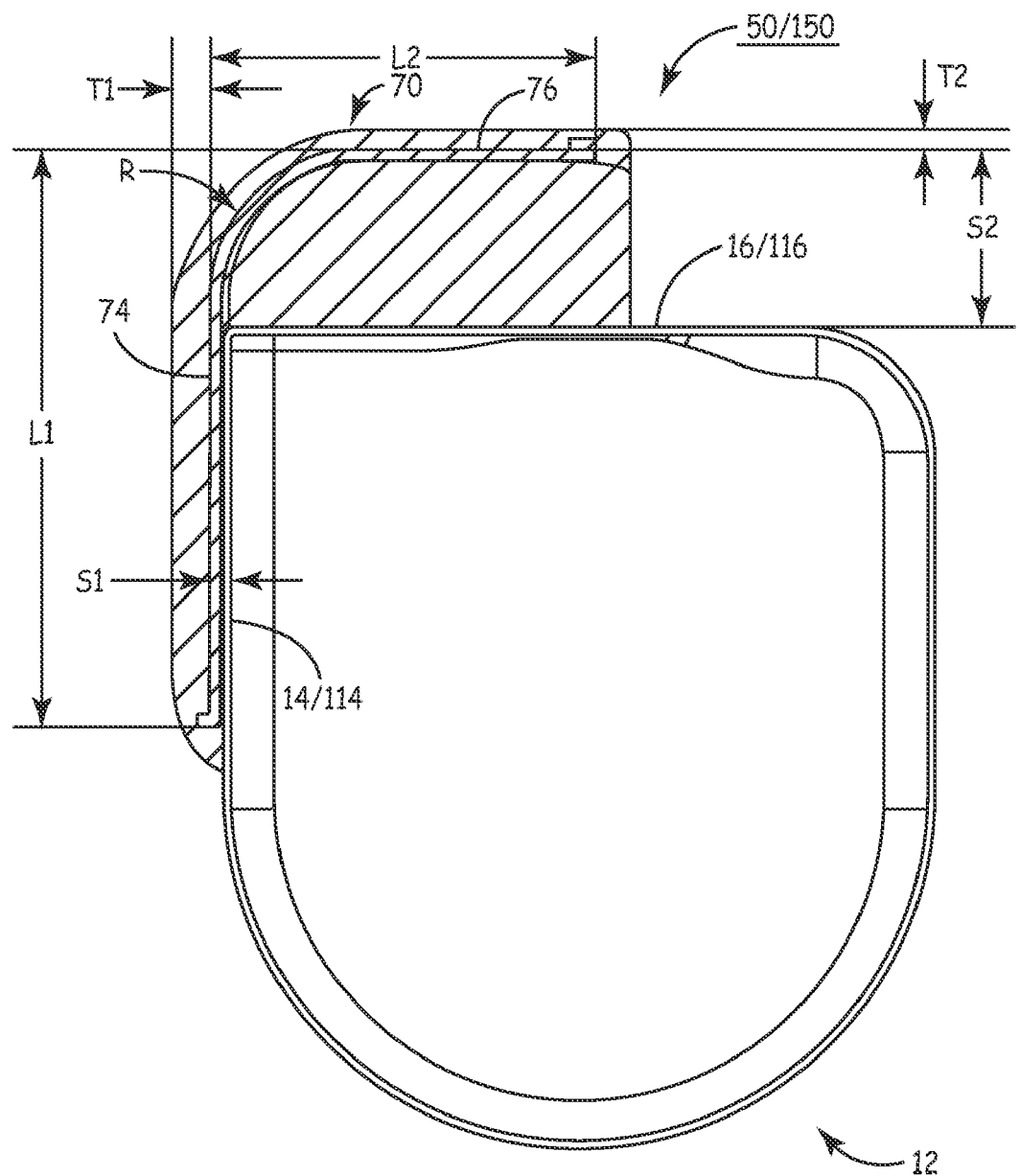
FIG. 10 is a schematic dimensional illustration of the orthogonal disposition of the first and second telemetry elements of the first and second embodiments with respect to the ICD housings.

FIG. 10 schematically illustrates the relative dimensions and spacing of the first and second antenna elements 74 and 76 within the first and second header segments 53 and 54, respectively, of the integral connector header 50 and within the first and second header segments 153 and 154, respectively, of the composite connector header 150.

The first antenna element 74 has a first length L1 within the first header segment 53, 153 and is supported to extend substantially parallel to and at a first side spacing S1 from a first minor side 14 of the hermetically sealed housing 12. The length dimension L1 is related to the available length of the first minor side 14. Similarly, the second antenna element 76 has a second length L2 within the second header segment 55, 155 and is supported to extend substantially parallel to and at a second side spacing S2 from the second minor side 16. The second side spacing S2 is dictated in part by the dimensions of the connector elements.

The dielectric overmold material of the overmold between the first antenna element 74 and the outer surface of the first header segment 53, 153 has a first radome thickness T1 that provides a radome over the first antenna element 74. The dielectric overmold material of the overmold between the second antenna element 76 and the outer surface of the second header segment 55, 155 has a second radome thickness T2 that provides a radome over the second antenna element 76. The radome thicknesses T1 and T2 can be theoretically calculated and empirically confirmed or adjusted so that the antenna 70 is tuned for optimal reception and transmission at the nominal 403 MHz carrier frequency operating within body tissue over the specified range.

In one example, the IMD telemetry antenna 70 is constructed as a flat titanium wire that is 0.010 inches thick, 0.025 inches wide, and 3.04 inches long overall. The side spacing S1 can be set to between 0.040 and 0.050 inches, for example, and the side spacing S2 can be set to between 0.480 and 0.500 inches, for example. The radome thicknesses T1 and T2 can be set to about 0.020 inches. Reliable telemetry transmission and reception over a distance of at least two meters at the nominal 403 MHz carrier frequency operating within air and body tissue between the IMD telemetry antenna 70 and an EMD telemetry antenna is partly provided by these IMD telemetry antenna preferred embodiments of the invention.

This antenna design meets the system requirements for the two meter minimum range and provides adequate gain, gain pattern, bandwidth, and tunability using one or more reactive element for different possible environments before and after implanting of the IMD, particularly for implantation in muscle layers. The polarization of the IMD telemetry antenna 70 becomes circular in muscle and close to linear in fat. The polarization depends on the environment that the IMD is located in. The polarization is close to linear when the IMD is in an environment of a relatively low permittivity and low conductivity, e.g., air or body fat. The polarization is ellipsoidal or circular in muscle because the permittivity and conductivity of muscle is much higher, which results in a shorter wavelength than the wavelength would be in air. This is especially the case for the main lobe of the gain pattern.

To implement effective telemetry from a given IMD over the distances desired, the driving power should be efficiently converted to maximize the far-field component generated by the antenna. One factor affecting the far field component is the length of the antenna with respect to the wavelength of the driving signal. While many types of antennas function according to a variety of parameters, it is generally desirable to provide an antenna having a minimum length equivalent to one-quarter or one-half the wavelength of the driving frequency. Longer lengths generally provide better performance and the overall length is preferably an integral multiple of the half wavelength of the driving frequency. Other factors include the dielectric values imposed by the surrounding medium (e.g., housing, header, human tissue) and the external environment (e.g., air).

Thus, the following embodiments provide for telemetry antennas having a longer length, as compared to previous embodiments while remaining substantially external to the housing. In addition, the following embodiments provide such an antenna without expanding upon the size of the connector header and without requiring an additional volume of dielectric material.

Figure 11A:
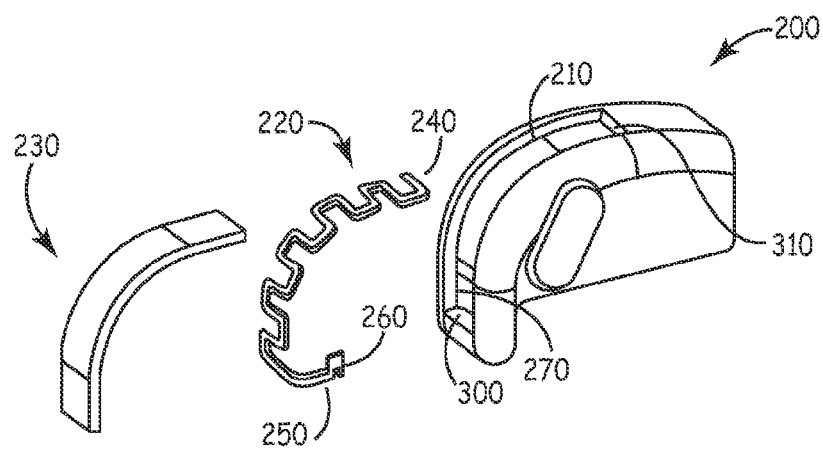
FIG. 11A is an isometric, exploded view of a header assembly and a serpentine antenna.
Figure 11B:
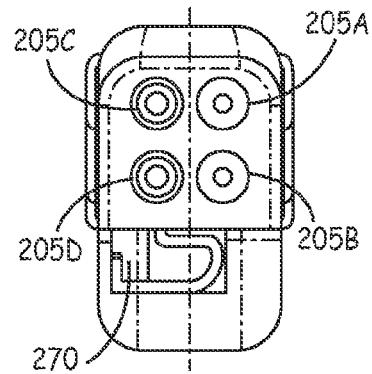
FIG. 11B is a front elevational view of the header and serpentine antenna of FIG. 11A.
Figure 11C:
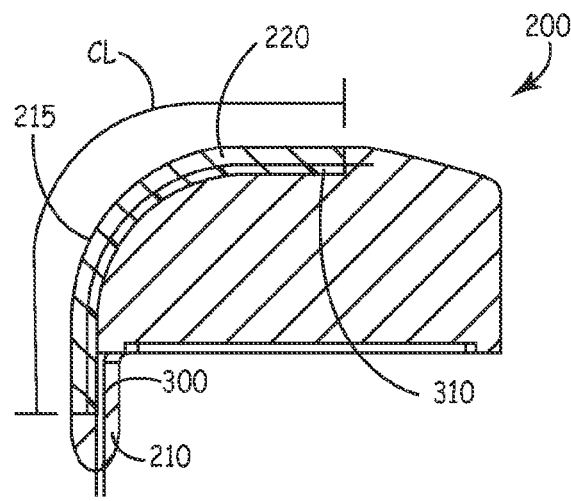
FIG. 11C is a side elevational view of the header and serpentine antenna of FIG. 11A.

Referring to FIGS. 11A-11C, a connector header 200 is illustrated. Connector header 200 is similar to the above-described header 50 in terms of function and construction, but does not include an extended elongated portion that extends along a lateral sidewall of the housing 10 to encase the antenna 70.

Connector header 200 is coupled with the housing 12 in the same manner as previously described, though housing 12 is not illustrated in FIGS. 11A-11C for clarity. Connector header 200 includes one or more connector ports 205 for receiving external component attachments such as a lead. Depending upon the type of IMD in question, the size, shape and configuration of the connector header 200 may vary. For example, the number and arrangement of connector ports 205 may vary.

A channel 210 is defined within the header 200 and antenna 220 is received within the channel 210. A cover 230 is disposed over the antenna 220 and seals the channel 210. The antenna 220 includes a proximal end 250 and a distal end 240. When assembled, the majority of the antenna 220 is contained within the header 200. A connector tab 260 depends from the proximal end 250 and projects through an interior opening 270 within the header 200. The connector tab 260 then makes electrical contact with terminals in communication with the telemetry transceiver disposed within the housing.

As previously indicated, one factor to consider for far field telemetry is the length of the antenna 220. The channel 210 defines a constraining length CL as the linear path between a proximal end 300 and a distal end 310 of the channel 210 while following the contour of the channel 210. The channel 210 is not limited to the shape, location, and relative length illustrated; but, however, the channel 210 (or space dedicated to the antenna) is ultimately defined provides for the constraining length CL. As such, a linear, straight-line antenna (such as antenna 70 in FIG. 4) would not have an antenna length that exceeds the constraining length CL. In the present embodiment, the antenna 220 has an antenna length that is greater than the constraining length CL. This is accomplished by providing a serpentine arrangement to the antenna 220.

Figure 12A:
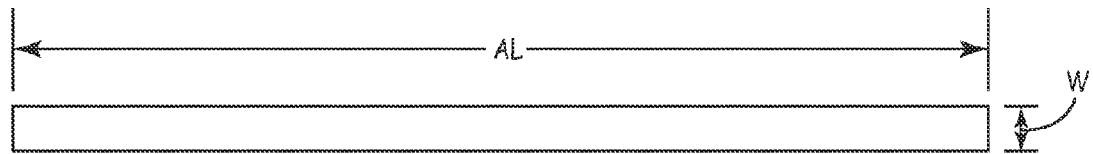
FIG. 12A is a schematic illustration of a linear substrate.

Referring to FIGS. 12A-12F, the serpentine arrangement is illustrated with respect to a generic antenna substrate 400. FIG. 12A is top planar view of the substrate 400, which is a flat and linear component having a rectilinear cross section. In this configuration, the actual linear length of the substrate 400 is equal to the antenna length AL. The width W of the material is also indicated. It is the antenna length AL that is relevant to determining the operability and effectiveness of a given antenna in a given system. To utilize the substrate 400 in the illustrated form, a space must be provided that has a length equal to or greater than the antenna length AL. For example, referring to FIG. 11A, the antenna length AL of substrate 400 would have to be less than the constraining length CL to utilize the straight substrate 400 as an antenna in the header 200.

Figure 12B:
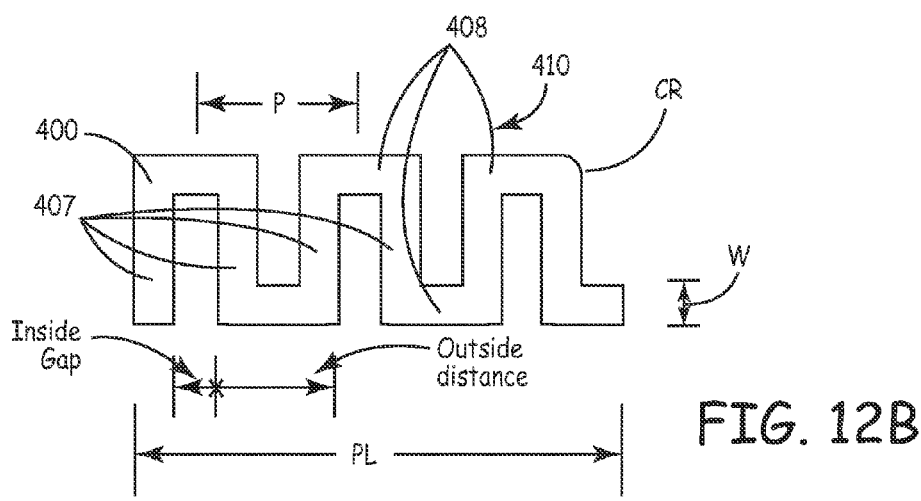
FIGS. 12B-12J are schematic illustrations of serpentine antenna configurations.

FIG. 12B illustrates a serpentine arrangement that is approximately to scale with the substrate 400. The serpentine antenna 410 has the same antenna length AL as the substrate 400 as well as the same width W of the material; however, because of the serpentine configuration the product length PL of the antenna is shorter than the antenna length AL. As such, the serpentine antenna 410 can be accommodated in the header channel 210 having a constraining length CL that is less than the antenna length AL. Of course, the product length PL is equal to or less than the constraining length CL. In the example illustrated, the antenna width AW of the serpentine antenna 410 is greater than the material width W. Thus, the channel 210 must have a width sufficient to receive the antenna 410, having width AW which is defined by the serpentine configuration.

There are a number of variables that affect the geometry of the serpentine antenna 410. Initially, the overall material length or antenna length AL is selected accordingly. The desired antenna width AW is also determined. Considerations include, for example, the volume of the available space within the header 200. The pitch P is defined as the distance between two subsequent, similar points, e.g., peak to peak as illustrated. The smaller the pitch P, the longer the antenna length AL for a given constraining length CL. As both the pitch P and material width W approach zero, the maximum length for a given antenna width is approached. In practice, the minimum pitch P selected should be sufficient to maintain the antenna characteristics of an antenna having a length AL. As illustrated, the serpentine pattern defines an inside gap and an outside distance. As the inside gap reaches zero, the antenna length AL becomes the product length PL. That is, the benefits gained by the serpentine pattern are rendered null if there is no differential (e.g., contact occurs) between at least some of the adjacent sections. Conversely, as the pitch becomes very large, the antenna or at least large portions thereof approximate or become linear.

The pitch P can be varied to increase or decrease the product length of the antenna 410. The pitch P does not need to be uniform over the entire antenna 410 and can be varied in any number of ways. For example, linear sections or sections having various curvilinear patterns may be used to position the antenna within the header 200 in the desired configuration.

For illustrative purposes, the two dimensional representations in FIGS. 12A and 12B are shown as rectilinear substrates having perpendicular adjoining sections. Alternatively, the inside and/or the outside corners may be radiused as illustrated by the corner radius CR. The selection of appropriate corner radiuses permits smaller pitches in certain embodiments. Alternatively, rather than providing perpendicular adjoining sections, the serpentine pattern could be sinusoidal or approximate various other curvilinear patterns. The material width W can be reduced relative to the other dimensional variables to facilitate the manufacture of an antenna having a relatively small pitch. As illustrated, the material width W is relatively large in comparison to the product length PL and a smaller width in practice will allow for a tighter pitch.

The serpentine antenna 410 is continuous structure, but a plurality of definable portions may be identified to illustrate certain concepts. It will be appreciated that various terms utilized to indicate direction and orientation with respect to FIG. 12B are for illustrative purposes only and are not meant to be limiting. For example, the serpentine antenna 410 includes a plurality of vertical antenna segments 407 and a plurality of horizontal antenna segments 408. The vertical antenna segments 407 are linear, have a uniform length, and are parallel to one another. The vertical antenna segments 407 are interconnected in an alternating end-to-end configuration (to form the continuous serpentine path) by the horizontal antenna segments 408, which are also linear, have a uniform length, and are parallel. The horizontal antenna segments 408 are perpendicular to the vertical antenna segments 407.

Figure 13A:
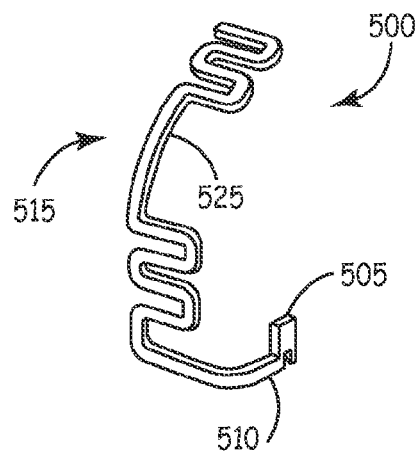
FIGS. 13A-13F are illustrations of various serpentine configurations for an antenna.
Figure 13B:
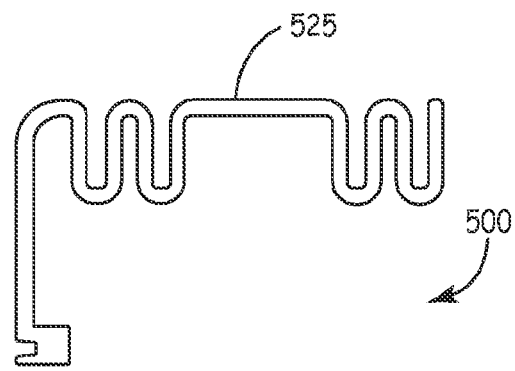

Many variations of the serpentine configuration presented herein can be expressed in terms of defining the antenna segments 407, 408. Increasing or decreasing the length of either type of segment 407, 408 will affect the overall antenna length. Rather than having linear portions interconnected at right angles, the horizontal segments 408 may be replaced with arc segments (e.g., FIG. 13A). Typically, the length of the vertical segment(s) 407 (product width direction) would then be greater than the length of the arc segments (product length direction). The arc dimensions would then dictate the pitch, assuming the vertical segments 407 are linear and parallel. The vertical segments 407 could be linear and non-parallel. In such an embodiment, the offset angle as well as the length of the segment would affect the pitch. Finally, the linearity could be removed, resulting in a sinusoidal configuration.

Figure 12C:
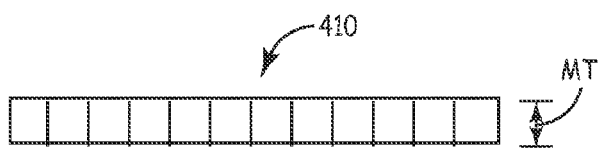
Figure 12D:
Figure 12E:
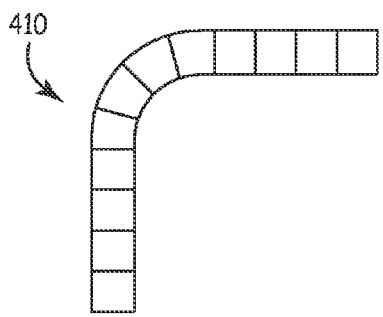

Up to this point, we have adjusted the "path" of the antenna in a two dimensional plane so as to increase the antenna length AL relative to the product length. FIG. 12C is a side elevational view of the serpentine antenna 410 having a thickness MT while FIG. 12D is an end view having the same thickness. From both of these perspectives, the serpentine antenna 410 is linear or in other words, flat. In practice, the antenna 410 can be non-linear in one or both of these planes in addition to having the serpentine configuration. Such additional modification serves various purposes. First, the fabricated antenna 220 can follow a curvilinear path defined by the channel 210 (FIG. 11A). In other words, the antenna 410 is not limited to planar installation. This is illustrated in FIG. 12E, which is a side elevational view of the serpentine antenna 410 having a curved side profile, such as that of antenna 220. With curvature in this profile, the end view would still correspond to that illustrated in FIG. 12D. Such is also the case with the embodiment illustrated in FIG. 11A, wherein the antenna 220 has a serpentine planar profile, a curvilinear side profile, and a flat end/cross sectional profile with respect to the serpentine portion.

Figure 12F:

FIG. 12F illustrates the end view of serpentine antenna 410 having a curvilinear cross sectional or end profile. Such a profile would be beneficial, for example, if the channel 210 did not have a planar surface, but rather was arcuate. In addition, curvature in this dimension allows for an antenna to have an antenna width AW that is larger than a given linear channel width (e.g., channel 210).

In addition to providing curvilinear side and/or cross sectional profiles to correspond to the channel 210, such curvilinear configurations further increase the antenna length AL. That is, the shortest distance between any two points is a straight line; as such any arc connecting the same two points necessarily represents a longer distance. FIGS. 12E and 12F illustrate a representative curvature and present the serpentine antenna 410 having the same dimensions as in FIGS. 12C and 12D, respectively. Thus, simply making a linear component 12C and 12D) curvilinear (FIGS. 12E and 12F) does not increase its the length; however, it is the path within the header 200 that defines the relevant consideration. That is, by defining the channel 210 to require or accommodate curvilinear profiles in the relevant planes, longer antenna lengths are permitted, as compared to straight-line paths between the same points in the header 200. In summary, the serpentine arrangement and providing a curvilinear profile each separately add length to the antenna. The present invention provides an antenna having dimensions that exceed an otherwise absolute maximum dimensional limitation (e.g., constraining length, width, etc.) by geometrically transferring dimensional attributes from a constrained dimension to dimension having capacity. For example, the serpentine arrangement transfers antenna length to a width dimension.

Figure 12G:
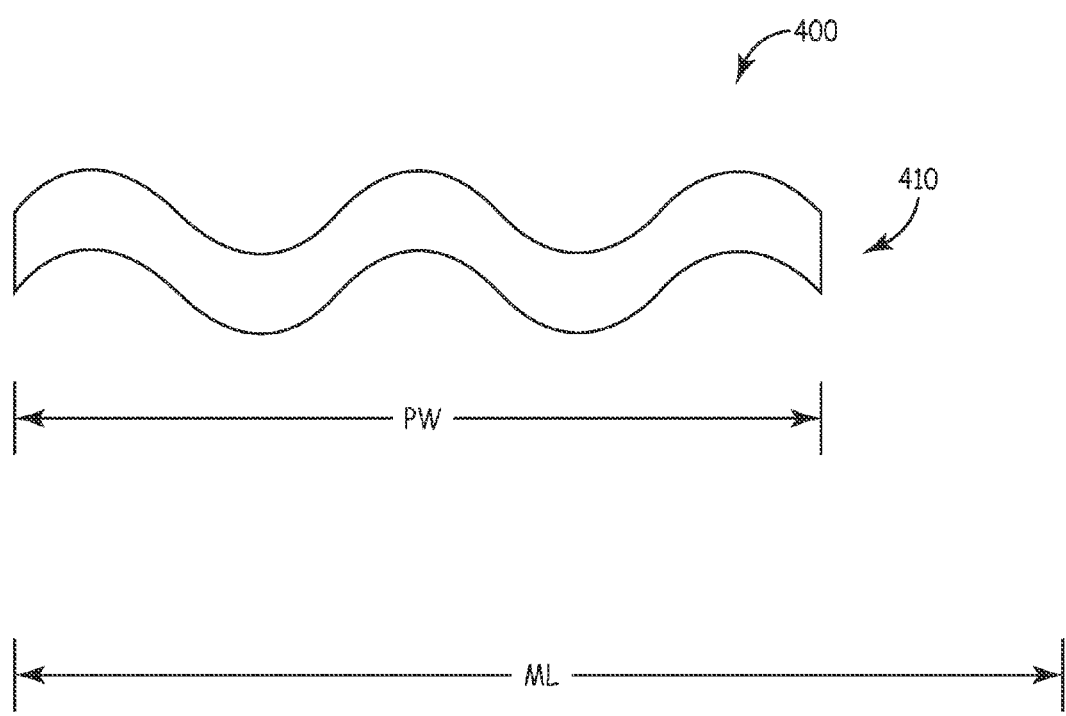

FIG. 12G illustrates how a curvilinear end or cross sectional profile adds such length to an antenna. In this end view of antenna 410, a sinusoidal geometry is provided, wherein the serpentine pattern projects perpendicularly into the page. As illustrated, the product width PW is shorter than the material length ML, wherein the material length is the length of the illustrated end if "flattened.". While a sinusoidal pattern is illustrated, it should be appreciated that any curvilinear path may be employed. Once again, the dimensional limitations of the header 200 and more particularly the channel 210 provide a maximum width or constraining width that limits the product width PW of an antenna. By utilizing other available space within the header 200, additional length can be provided in this manner.

Figure 12H:
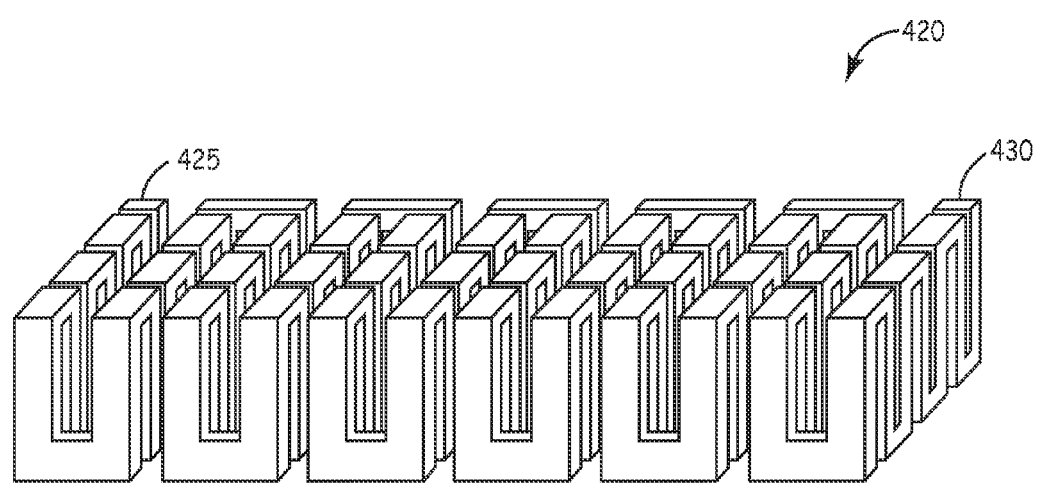

The serpentine pattern may be replicated in three dimensions to achieve even greater antenna length AL within a given volume. FIG. 12H illustrates a three dimensional serpentine antenna 420. As illustrated, the antenna 420 is a continuous structure having a first end 425 and a terminal end 430. The same variables previously discussed, such as pitch, material dimensions, and corner curvature/radius may be manipulated to increase or decrease the antenna length AL within a given volume. It should also be appreciated that the illustrated embodiment provides an example of uniform patterning. By reducing the compactness of this structure by, e.g., utilizing linear portions to increase selected gap distances, more antenna surface area is exposed, which may be desirable depending upon the specific antenna and telemetry parameters employed.

Figure 12I:
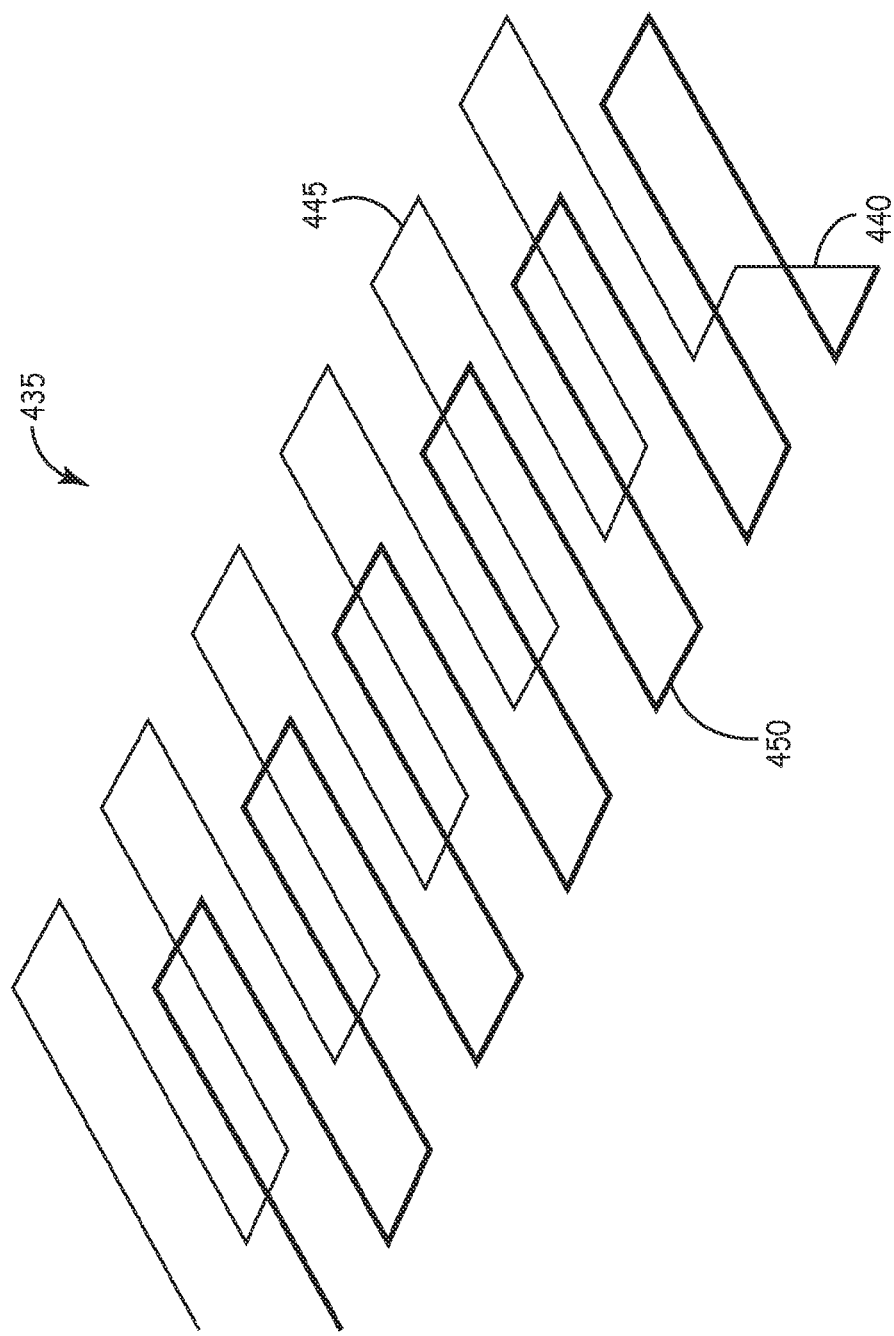

Referring to FIG. 12I, another serpentine antenna 435 is illustrated. Antenna 435 includes the serpentine configuration discussed with respect to FIG. 12B and includes the same ability to vary the parameters such as, for example, pitch, material dimensions, and corner curvature. A first antenna section 445 is disposed in a first plane while a second antenna section 450 is disposed is a second plane, spaced from the first. In other words, one or more serpentine sections are layered within the header 200. Again, this permits the antenna length AL to be increased within a given volume of available space within the header 200. In addition, the antenna 435 may be bifurcated at midpoint 440 to act as a dipole antenna. Any number of layers may be utilized so long as sufficient antenna performance is realized.

While certain geometrical configurations have been illustrated, they should not be taken as limiting. Furthermore, more complex geometries employing the illustrated principles may also be incorporated. For example, the serpentine portions of a given antenna could form fully or partially looped, three dimensional geometries within the available volume. Conceptually, the two dimensional serpentine arrangement (e.g., FIG. 12B) could be "wrapped" about the perimeter of a parallelepiped, cylinder, or other three-dimensional volume.

Referring again to FIG. 11B, the header 200 includes a variety of structural components such as the connectors 205. For a given header 200, these structural elements define the free space available to position the antenna 220. In the illustrated embodiments, the channel 210 is provided near an upper surface (as illustrated) of the header 200 and generally positions the antenna 220 over/behind (as illustrated) these components.

Figure 12J:
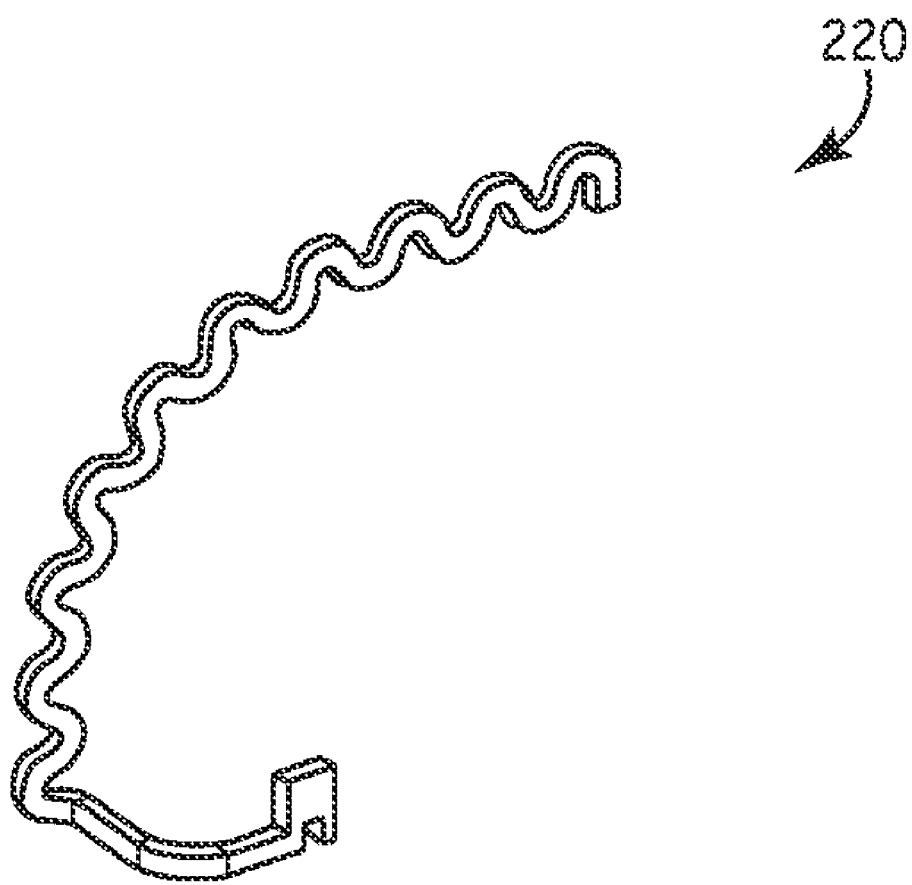

The antenna 220 can be positioned anywhere within the header 200 with respect to these various components. For example, the connectors 205 are individually designated as 205A-205D. In the illustrated embodiments, the relevant portion of the antenna 220 is positioned above connectors 205A and 205C. Alternatively, the antenna 220 could be positioned in the horizontal plane below 205A and 205C and above 205B and 205D or in the horizontal plane below connectors 205B an 205D. Furthermore, the antenna 220 could be modified so that the serpentine portions extend vertically rather than horizontally (with respect to FIG. 11) or at any angular offset. For example, the antenna 220 could be disposed in a vertical plane between the connectors 205 or on either side thereof. FIG. 12J illustrates antenna 220 having a vertical serpentine configuration. The antenna 220 may be disposed medially within the header 200 or closer to a given side. In addition, the length of the serpentine segments may be selected so as to cover any depth desired within the header. Of course, any other components disposed within the header 200 may affect positioning; however, the antenna 220 may be positioned in various orientations and situated anywhere within the volume of the header 200. The header 200 may be designed to accommodate a given antenna 220 or the antenna 220 may be adapted to a preexisting header design.

As indicated, various other components or hardware may be disposed within the header 200 that might hinder an otherwise desirable antenna placement. In some cases, the header 200 may be redesigned or modified to accommodate the antenna placement. Alternatively, a different antenna position may be selected. A third alternative is to utilize a serpentine antenna 220 having a varying pitch to avoid the component(s) at issue.

FIGS. 13A-13F illustrate a serpentine antenna 500 having portions with differing pitch. Similar to the previous embodiments, antenna 500 includes a connector tab 505 and an interconnect portion 510 that interconnect the main portion of the antenna 500 with the appropriate terminal on the transceiver disposed within the housing. The specific configuration of these portions will vary based on the distance, location, and type of connection to be made.

The antenna 500 includes a lower serpentine portion 515 and an upper serpentine portion 520. A medial portion 525 connects the upper and lower serpentine portions 515, 520. The medial portion 525 is illustrated as being linear (infinite pitch) from a top planar perspective, illustrated in FIG. 13B. As such, if some component was present in the channel 210 or prevented the channel 210 from having a sufficient width in a particular area, the medial portion 525 could be shaped and positioned to avoid the component or narrowed region. By reverting to a linear path, antenna length is reduced; however, the pitch, antenna material dimensions, antenna width, and corner radii can be selected for the upper and lower serpentine portions 515 and 520 so that the overall antenna length is appropriate. Medial portion 525 is illustrated as being linear, however other configurations are also possible. For example, medial portion 525 may be non-linear or may be serpentine and simply vary in pitch from the remaining serpentine portions. That is, the medial portion 525 can take any form appropriate to avoid an obstruction, change the direction/orientation of one portion of the antenna 500 from another, follow a given path, or to enhance or modify performance.

Figure 13C:
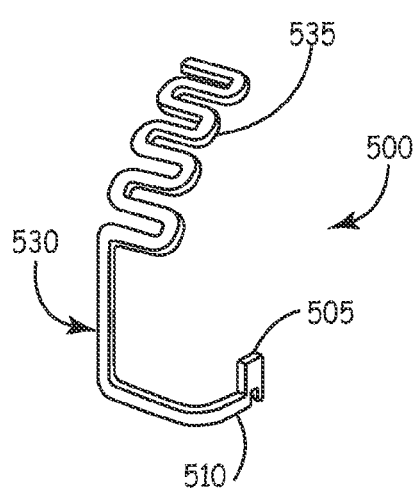
Figure 13D:
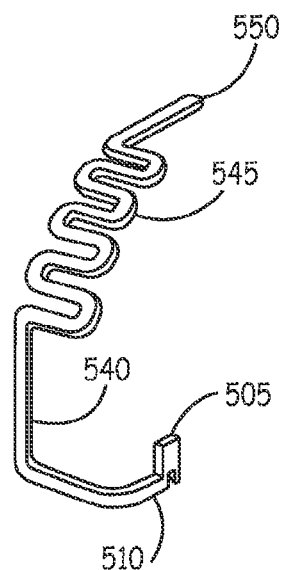
Figure 13E:
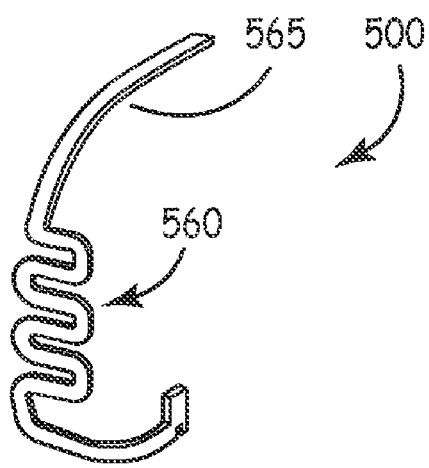
Figure 13F:
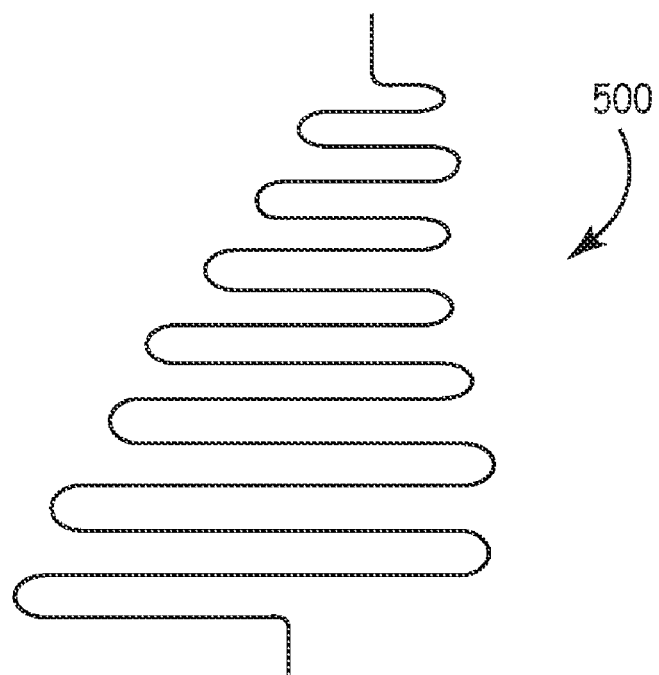

FIG. 13C illustrates the antenna 500 having a lower linear portion 530 and an upper serpentine portion 535. FIG. 13D illustrates an embodiment wherein antenna 500 includes a lower linear portion 540, a medial serpentine portion 545, and an upper linear portion 550. The antenna 500 of FIG. 13E includes a lower serpentine portion 560 and an upper linear portion 565. Once again, the illustrated embodiments are not meant to be limiting. Any linear section may be replaced with a curvilinear or serpentine section having a pitch that results in an appropriate configuration based on the spatial constraints of the header. In addition, with any of the embodiments discussed herein, the pitch over a given serpentine section has been illustrated as being constant; however, the pitch may be varied within a given section as desired. Finally, antenna width, defined by the serpentine portions has also generally been illustrated as being uniform. This width may also be varied while remaining within the scope of the present invention. One such pattern is schematically illustrated in FIG. 13F.

In addition to physically avoiding structural components, another consideration for the placement of antenna 220 is visually obscuring certain components. For example, header 200 often is fabricated from a material having certain translucent characteristics. Thus, an implanter can visually verify that given lead pin is fully inserted within a given connector 205. As such, the above noted variations may be employed to create or maintain a visual window.

Returning to FIGS. 11A-11C, the antenna 220 is illustrated as a separate component that is coupled with the header 200. Antenna 220 may be fabricated from any appropriate material, including conductive metals, such as, for example, titanium and titanium alloys. To fabricate the antenna 220, raw material may be taken from a linear form and bent into the desired configuration. For example, wire having a cylindrical cross section is well suited for such a bending process.

The antennas 220 in the various illustrated embodiments utilize a material having a rectilinear cross section. While not required, such material allows for a difference between the width and thickness of the material. That is, the area of the outwardly radiating surfaces can be increased relative to the area of the lateral edge(s). Furthermore, the material may provide more rigidity and/or structural integrity to the antenna 220. If raw material having a rectilinear cross section is utilized, it to may be bent to fabricate the antenna 220.

Alternatively, the antenna 220 is formed from a stamping process wherein raw material is press formed into the appropriate configuration or by utilizing casting methods that are well known. Photolithography or other etching techniques may be employed and are particularly applicable to small scale, complex patterns. Generally, the antenna 220 is fabricated as a single unitary element; however, welding or other bonding techniques may be utilized to combine multiple components together. For example, connector tab 260 may be a separate element that is coupled with the remainder of the substrate to form a completed antenna 220. Multiple sections may be joined to form an antenna having a given length. Depending upon the fabrication techniques, the design parameters, and material selections, the antenna 220 may be formed into its final configuration during initial manufacture or a multi-step process may be implemented. For example, a linear substrate having the serpentine pattern may first be formed from, e.g., an etching process. That substrate may then be curved (e.g., the side profile illustrated in FIG. 11C) to complement the channel 210. Finally, the connector tab 260 and the relevant dependant portions may be appropriately angled or attached if separate.

FIG. 11C illustrates one embodiment wherein the antenna 220 is disposed within the channel 210. In this side elevational view, the antenna 220 is positioned near an upper surface (as illustrated) of the header 200. In addition, the antenna 220 is uniformly spaced from an exterior surface 215 of the header 200. As the header 200 is typically made from a dielectric material, the effect of such material on the antenna's properties is relevant. Furthermore, in actual use, the ICD 10 is implanted within human tissue having a relatively high dielectric value. With the illustrated embodiment, the distance from the antenna to exterior surface 215 is uniform and the exterior surface 215 itself is uniform; thus, contact with surrounding body tissue and fluids is even. Hence, the antenna 220 is also uniformly spaced from the header/tissue interface. In this embodiment, the antenna 220 is spaced about 50 mils from the exterior surface. In other exemplary embodiments the antenna 220 may be spaced from approximately 10-100 mils from the exterior surface. While illustrative, these embodiments are not limiting. The distance selected is based upon the specific parameters and performance requirements chosen for the antenna 220 and the transceiver utilized and may be greater or less than those of the exemplary embodiments.

One benefit of positioning the antenna 220 in header in the illustrated orientation is that telemetry performance will not be affected by the orientation of the ICD 10 when it is implanted. The ICD 10 will always be implanted such that a major plane of the device 10 projects outward from the patient. Depending upon the implantation site and the preferences of the physician, either major surface may face outward; however, the antenna performance will be the same regardless of which major surface faces outward or the rotational orientation of the device 10.

Figure 14A:
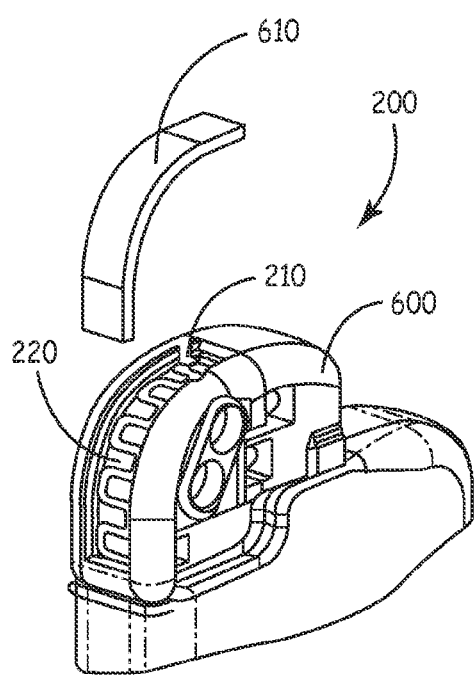
FIGS. 14A-14E illustrate a variety of antennas having serpentine configurations disposed within a header assembly.
Figure 14B:
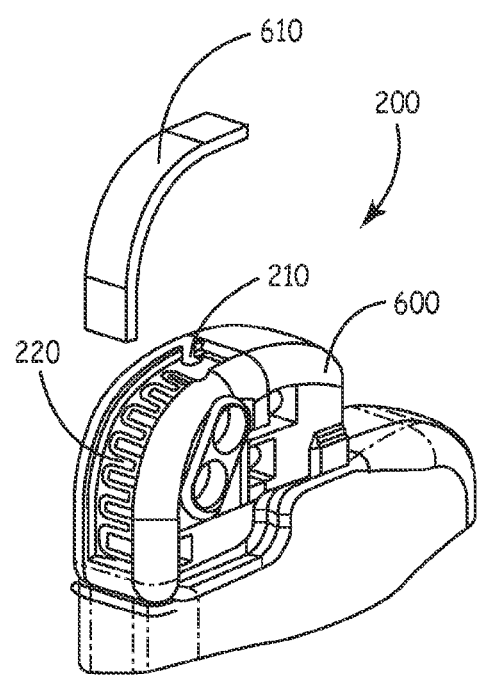

FIGS. 14A-14E show a variety of embodiments of the ICD 10, wherein the antenna 220 has varying geometrical configurations. Referring to FIG. 14A, one process of fabrication will be described. A main header section 600 is molded from an appropriate polymer and includes the various components previously indicated. More specifically, a header substrate is fabricated with the components. An encapsulating shell is the molded around the header substrate to form the main header section 600. Any number of known molding techniques may be utilized to mold the main header section 600. As part of this molding process, the channel 210 is formed. The completed antenna 220 is placed within the channel 220 so that the connector tab 260 passes through the interior opening 270 (FIGS. 11A, 11B). The connector tab 260 is coupled with the appropriate terminal and secured when the header is coupled with the housing. This may be accomplished with welding or otherwise bonding the tab 260 to the terminal or the components may be shaped to generate a frictional or clamping arrangement.

Once the antenna 220 is positioned within the channel 210, a cover 610 is placed over the channel 210 and sealed. Generally, the cover 610 will hermetically seal the antenna 220 within the channel 210. Various techniques may be employed to seal the cover 610. For example, the cover 610 may be bonded with an adhesive to the main header portion 600 or may be heat-sealed. Additionally, once the cover 610 is in place a secondary layer or overmolding may be molded over the main header 600 and the cover 610 to form a uniform, sealing barrier (not separately shown). Alternatively, the main header portion 600 may be subjected to a secondary molding process after the antenna 220 is placed within the channel 210. That is, rather than pre-forming a cover 610, raw material is directed into the channel 210 and appropriately retained and shaped. This staged molding process is utilized to fabricate the completed header 200. With this process, the antenna 220 is completely encased and secured within the header 200. A secondary sealing layer may also be molded or otherwise fabricated over some portion of or the entirety of the header 200.

Figure 14C:
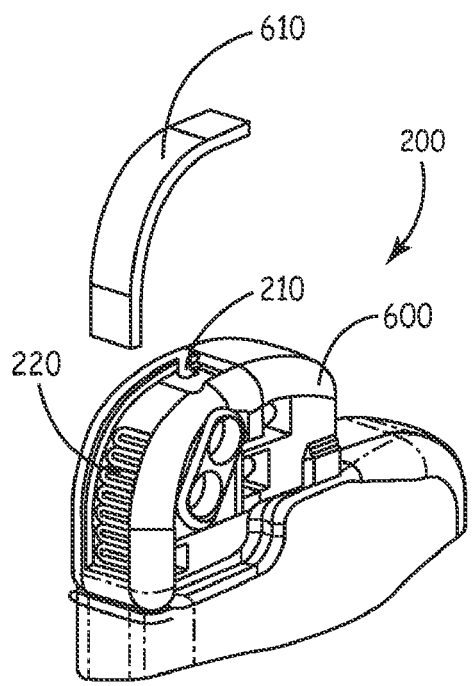
Figure 14D:
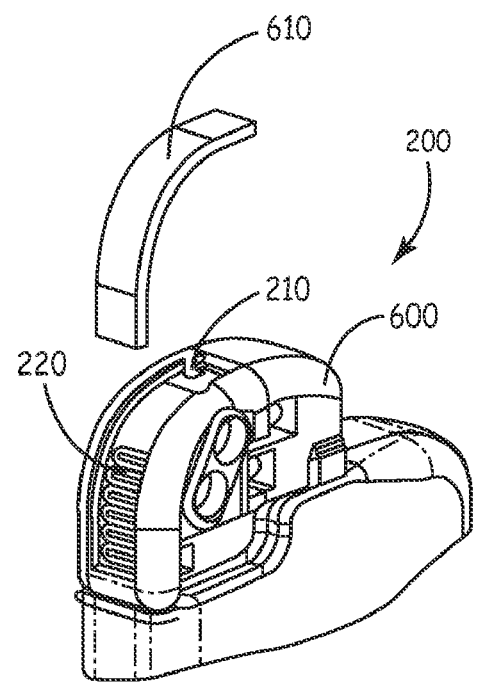
Figure 14E:
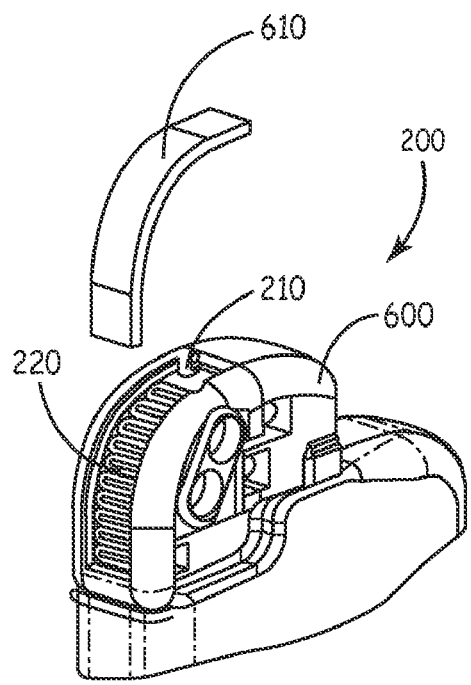

FIGS. 14A-14E illustrate a variety of configurations for antenna 220. In FIG. 14A, antenna 220 has a uniform serpentine pattern over the majority of the structure within the channel 210. In addition, the product length PL is approximately equal to the channel length CL. That is, the antenna 220 extends over the whole length of the channel 210. The pitch of the antenna 220 is larger in comparison to the embodiments of FIGS. 14B-14E. The antenna 220 of FIG. 14B has a smaller pitch and extends along approximately 75% of the channel 210. FIGS. 14C and 14D illustrate antennas 220 having progressively smaller pitches and extending over approximately half the channel length. Finally, FIG. 13 illustrates antenna 220 having a relatively small pitch and extending over the entire channel length.

In one embodiment, antenna 220 is fabricated from titanium and has a cross sectional thickness of 20 mils and a cross sectional width of 30 mils. In another embodiment, the titanium has a cross sectional thickness of 16 mils and a cross sectional width of the 20 mils. The overall antenna length AL varies from almost zero to any length that may be placed within the volume of the header 200. In certain embodiments, the antenna length is between 0.5 and 10 inches, in other embodiments the antenna length is between 2 to 3 inches, and in other embodiments, the antenna length is approximately 2.75 inches, and in another embodiment, the antenna length is 68 inches. As previously discussed, the actual antenna length desired will depend upon various transmission factors such as the frequency of the driving signal. The pitch of the serpentine portions may be generally uniform or may vary over a given antenna. Pitches for various embodiments range from almost zero, with an extremely small separation distance between adjoining portions, to infinite pitch for linear portions. In certain embodiments, the pitch of serpentine antenna portions ranges from 0.01 inches to 0.5 inches and in other embodiment the pitch ranges from 0.060 inches to 0.25 inches. In certain embodiments using titanium with the above-described dimensions, pitches of 0.064 inches, 0.080 inches, 0.124 inches, and 0.228 inches were selected.

Figure 15:
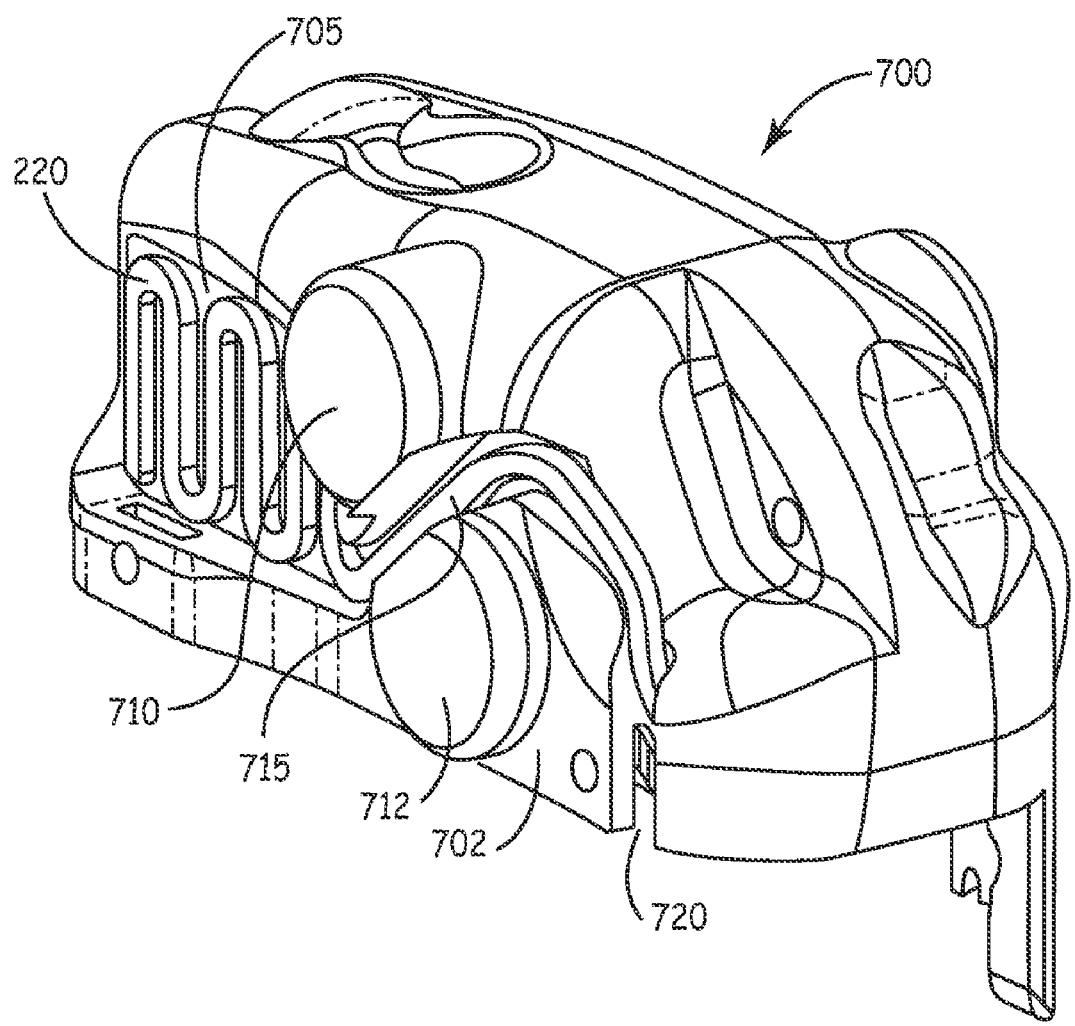
FIG. 15 is an isometric view of a header assembly having a serpentine antenna coplanar with a sidewall of the header assembly.

FIG. 15 illustrates another embodiment of serpentine antenna 220. In this embodiment, the antenna 220 is oriented in a vertical plane (as illustrated). More particularly, the antenna 220 is attached to or positioned against sidewall 702 of a header substructure 700. The sidewall 702 includes an antenna area 705 that is generally devoid of obstruction so that the serpentine portion of the antenna 220 abuts or remains close to the sidewall 702. The header substructure 700 includes two set screw ports 710, 712. An interconnecting portion 715 of the antenna 220 has a curvilinear geometry so as to pass between the setscrew ports 710, 712 and enter an antenna receiving channel 720, which allows access to the appropriate connection terminals. Once so configured, an appropriate material is molded over the header substrate 700 and the antenna 220 thus forming a completed header 200.

The antenna 220 may be varied in any of the above described ways to modify the antenna length or other parameters. In addition, a second such antenna 220 may be disposed on an opposite side of the header substrate. In such an embodiment, at least one antenna 220 would face outwards from the patient regardless of device orientation at implant. While one specific configuration has been illustrated, it should be appreciated that the specific antenna configuration will vary depending upon the location of the antenna area 705 relative to the channel 720 (or alternative means or interconnecting the terminal) and any surface obstructions that may be present in various header configurations. The path of the antenna 220 is not limited to any of the illustrated embodiments. For example, though not illustrated, the embodiments of FIG. 11A and FIG. 15 may be combined so that the antenna forms a serpentine path over an upper portion (as illustrated) of the header substrate 700 and one or both sidewalls 702.

Figure 16A:
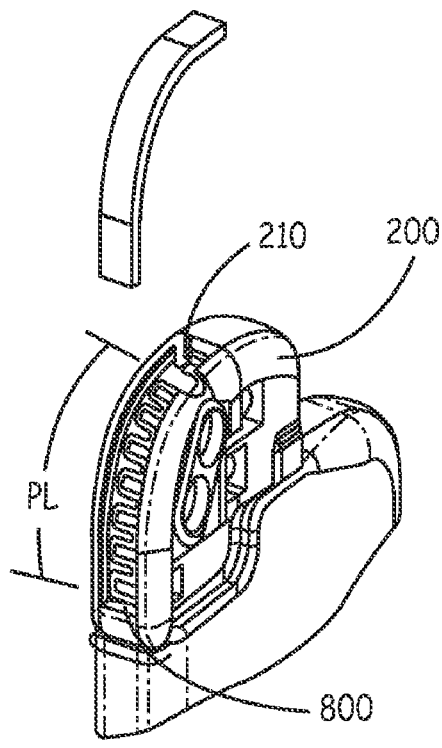
FIGS. 16A-16B illustrate a header assembly with antennas having a helical profile.
Figure 16B:
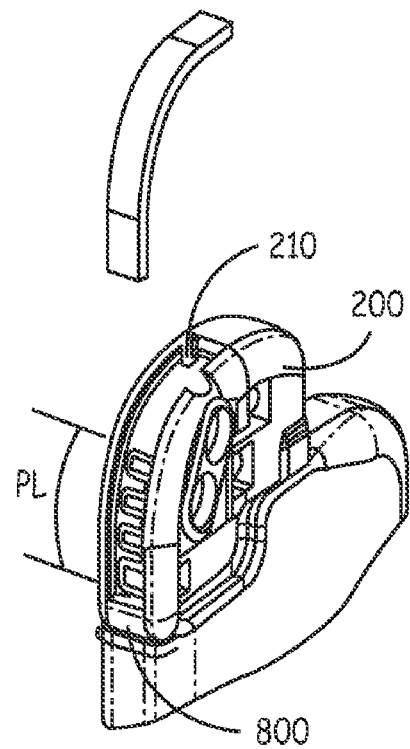

FIGS. 16A and 16B illustrate yet another embodiment of the present invention. An antenna 800 having a helical geometrical profile is disposed within the channel 210. The non-linear, helical path allows for an extended antenna length relative to the product length. The pitch of the helix is selected to provide the desired overall antenna length. FIG. 16A illustrates a helical antenna 800 with a larger pitch and thus a longer product length than the antenna 800 of FIG. 16B, though the antenna length for each is the same.

The various serpentine and curvilinear antennas 220 generally facilitate the use of an antenna structure having a longer antenna length AL than would otherwise be permissible in a standard header. If desired, even longer antenna lengths may be achieved by utilizing the serpentine antenna configuration with the larger connector header 50 (FIG. 1). In other words, the various serpentine antennas are advantageously utilized with standard header configurations but are not so limited. For any given header volume, the antenna structures of the present invention can be configured to achieve an increased or maximized antenna length.

It is therefore to be understood, that within the scope of the appended claims, the invention may be practiced otherwise than as specifically described without actually departing from the spirit and scope of the present invention.

The invention claimed is:

1. An implantable medical device comprising:
a housing;
a header coupled with the housing; and
an antenna disposed within the header, wherein at least a portion of the antenna has a serpentine configuration.

2. The implantable medical device of claim 1, wherein the serpentine configuration is continuous and comprises a plurality of generally linear antenna segments interconnected in an alternating end to end configuration by arcuate antenna segments.

3. The implantable medical device of claim 1, wherein the antenna is evenly spaced from a side surface of the header.

4. The implantable medical device of claim 1, wherein the antenna is spaced at a distance of approximately 10-100 mils from a side surface of the header.

5. The implantable medical device of claim 1, wherein the antenna is spaced at a distance of approximately 50 mils from a side surface of the header.

6. The implantable medical device of claim 1, wherein the header is a connector header having at least one connector port.

7. The implantable medical device of claim 6, wherein a plane defined by the serpentine configuration of the antenna is disposed between a side surface of the header and the connector port.

8. The implantable medical device of claim 6 wherein a plane defined by the serpentine configuration of the antenna is disposed between the connector port and the housing.

9. The implantable medical device of claim 1, wherein the header is a connector header that includes at least two connector ports and a plane defined by the serpentine configuration of the antenna is disposed between a pair of the connector ports.

10. The implantable medical device of claim 1, wherein a plane defined by the serpentine configuration is generally parallel with a major wall of the header.

11. The implantable medical device of claim 1, wherein the antenna is disposed within a channel within the header, the channel having a constraining length that is shorter than an antenna length of the antenna.

12. The implantable medical device of claim 11, wherein the antenna length is between 1 to 4 inches.

13. The implantable medical device of claim 11, wherein the antenna length is between 2 to 3 inches.

14. The implantable medical device of claim 1, wherein the antenna includes multiple serpentine portions.

15. A telemetry antenna for an implantable medical device comprising:
a header coupled to a body of the implantable medical device:
the telemetry antenna disposed within a portion of the header and further including;
proximal end section having an antenna connector;
distal end opposite the proximal end section;
serpentine portion disposed between and forming a generally continuous antenna path between the proximal end section and the distal end, the serpentine portion including a plurality of first antenna segments interconnected in an alternating end-to end configuration by a plurality of second antenna segments.

16. The telemetry antenna of claim 15, wherein the first antenna segments are generally linear in at least one dimension and the second antenna segments are arcuate.

17. The telemetry antenna of claim 16, wherein a length of the first antenna segments is greater than a length of the second antenna segments.

18. The telemetry antenna of claim 16, wherein the first antenna segments are generally parallel to one another.

19. The telemetry antenna of claim 18, wherein a pitch of the serpentine portion is between approximately 0.01 inches and 0.05 inches.

20. The telemetry antenna of claim 18, wherein a pitch of the serpentine portion is between approximately 0.06 inches and 0.25 inches.

21. The telemetry antenna of claim 15, further comprising a second serpentine portion disposed between the serpentine portion and the distal end, wherein an interconnecting segment interconnects the serpentine portion with the second serpentine portion.

22. The telemetry antenna of claim 21 wherein the interconnecting segment is generally linear in at least one dimension.

23. The telemetry antenna of claim 21, wherein the interconnecting segment is curvilinear.

24. The telemetry antenna of claim 15, further comprising a distal segment interconnecting the serpentine portion and the distal end.

25. The telemetry antenna of claim 24, wherein the distal segment is linear in at least one dimension.

26. The telemetry antenna of claim 24, wherein the distal segment is curvilinear.

27. The telemetry antenna of claim 15, wherein the serpentine portion is formed from a substrate having a cross sectional width defining a major planar profile and a cross sectional height defining a product length planar profile and a product width planar profile, wherein the serpentine portion has a serpentine configuration in the major planar profile.

28. The telemetry antenna of claim 27, wherein the cross sectional width is greater than the cross sectional height.

29. The telemetry antenna of claim 27, wherein the serpentine portion has a linear configuration in the product length planar profile.

30. The telemetry antenna of claim 27, wherein the serpentine portion has a curvilinear configuration in the product length planar profile.

31. The telemetry antenna of claim 27, wherein at least a portion of the antenna has a linear configuration in the product length planar profile.

32. The telemetry antenna of claim 27, wherein at least a portion of the antenna has a curvilinear configuration in the product length planar profile.

33. The telemetry antenna of claim 27, wherein the serpentine portion has a linear configuration in the product width planar profile.

34. The telemetry antenna of claim 27, wherein the serpentine portion has a curvilinear configuration in the product width planar profile.

35. The telemetry antenna of claim 27, wherein at least a portion of the antenna has a linear configuration in the product width planar profile.

36. The telemetry antenna of claim 27, wherein at least a portion of the antenna has a curvilinear configuration in the product width planar profile.

37. The telemetry antenna of claim 27, wherein the substrate is titanium.

38. The telemetry antenna of claim 37, wherein the cross sectional width is approximately 30 mils and the cross sectional height is approximately 20 mils.

39. The telemetry antenna of claim 37, wherein an antenna length exceeds a product length and the antenna length is between 1-10 inches.

40. The telemetry antenna of claim 37, wherein an antenna length exceeds a product length and the antenna length is between 2-3 inches.

* * * * *

UNITED STATES PATENT AND TRADEMARK OFFICE
CERTIFICATE OF CORRECTION

| | | |
|---|---|---|
| PATENT NO. | : 7,317,946 B2 | Page 1 of 1 |
| APPLICATION NO. | : 10/797511 | |
| DATED | : January 8, 2008 | |
| INVENTOR(S) | : Len Twetan et al. | |

It is certified that error appears in the above-identified patent and that said Letters Patent is hereby corrected as shown below:

Col. 18, line 32 claim 15, delete "including; proximal" and insert in place there of --including; a proximal--.

Col. 18, line 33 claim 15, delete "connectors; distal" and insert in place there of --connector; a distal--.

Col. 18, line 34 claim 15, delete "section; serpentine" and insert in place there of --section; a serpentine--.

Signed and Sealed this

Thirteenth Day of January, 2009

JON W. DUDAS
*Director of the United States Patent and Trademark Office*